(12) United States Patent
McLeod et al.

(10) Patent No.: US 9,865,182 B2
(45) Date of Patent: Jan. 9, 2018

(54) FIBERS WITH SURFACE MARKINGS USED FOR CODING

(71) Applicant: Eastman Chemical Company, Kingsport, TN (US)

(72) Inventors: Andrew Ervin McLeod, Jonesborough, TN (US); Brian Douglas Seiler, Kingsport, TN (US); Scott Gregory Gaynor, Bristol, TN (US); Michael Joseph Pearce, Blountville, TN (US); Kevin Todd Barham, Kingsport, TN (US); James Andrew Dickenson, Johnson City, TN (US); Clarissa Tatum, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 22 days.

(21) Appl. No.: 15/225,872

(22) Filed: Aug. 2, 2016

(65) Prior Publication Data
US 2016/0379528 A1 Dec. 29, 2016

Related U.S. Application Data

(62) Division of application No. 14/748,865, filed on Jun. 24, 2015, now Pat. No. 9,442,074.
(Continued)

(51) Int. Cl.
*G09F 3/00* (2006.01)
*G01N 21/84* (2006.01)
(Continued)

(52) U.S. Cl.
CPC ............. *G09F 3/0297* (2013.01); *A24D 3/00* (2013.01); *A24D 3/04* (2013.01); *A24D 3/063* (2013.01);
(Continued)

(58) Field of Classification Search
CPC ...... G01N 21/84; G01N 33/365; G01N 33/36; G01N 2021/8444; A24D 3/04; A24D 3/00;
(Continued)

(56) References Cited

U.S. PATENT DOCUMENTS

| 951,147 A | 3/1910 | Porter |
| 1,721,564 A * | 7/1929 | Lawson ................. D07B 1/148 40/316 |

(Continued)

FOREIGN PATENT DOCUMENTS

| CN | 202298350 U | 7/2012 |
| JP | 2000314045 A | 11/2000 |

(Continued)

OTHER PUBLICATIONS

Office Communication notification dated Mar. 1, 2017 received in co-pending U.S. Appl. No. 14/748,841.
(Continued)

*Primary Examiner* — Tarifur Chowdhury
*Assistant Examiner* — Mohamed K Amara
(74) *Attorney, Agent, or Firm* — Jennifer R. Knight; Dennis V. Carmen

(57) ABSTRACT

Disclosed are fibers comprising one or more branded fibers which exhibit surface markings in a repeated pattern along the length of the branded fibers. The branded fibers can be incorporated into yarns or fiber bands to represent supply chain information of the yarns, fiber bands, and/or articles made from the yards or fiber bands. In a specific example, branded fibers can be incorporated into an acetate tow band The branded fibers can be recovered from a cigarette filter, the repeated pattern decoded, and supply chain information associated with the acetate tow used to make the cigarette filter, such as manufacturer, customer, ship to location, and even the acetate tow bale, can be obtained.

20 Claims, 12 Drawing Sheets

An image of an acrylic monofilament fiber engraved using a MACSA carbon dioxide laser.

Related U.S. Application Data

(60) Provisional application No. 62/018,182, filed on Jun. 27, 2014, provisional application No. 62/105,011, filed on Jan. 19, 2015, provisional application No. 62/164,135, filed on May 20, 2015.

(51) Int. Cl.

| | | |
|---|---|---|
| *G01N 33/36* | (2006.01) | |
| *G06K 9/62* | (2006.01) | |
| *G06M 11/00* | (2006.01) | |
| *D01G 15/46* | (2006.01) | |
| *G06K 7/10* | (2006.01) | |
| *G06K 19/06* | (2006.01) | |
| *G09F 19/00* | (2006.01) | |
| *D06P 5/00* | (2006.01) | |
| *D01D 5/08* | (2006.01) | |
| *D06M 23/16* | (2006.01) | |
| *D01D 5/36* | (2006.01) | |
| *D01F 1/04* | (2006.01) | |
| *D01F 1/06* | (2006.01) | |
| *D01F 2/28* | (2006.01) | |
| *G07D 7/12* | (2016.01) | |
| *A24D 3/04* | (2006.01) | |
| *G07D 7/2033* | (2016.01) | |
| *A24D 3/06* | (2006.01) | |
| *A24D 3/10* | (2006.01) | |
| *G06K 7/14* | (2006.01) | |
| *A24D 3/00* | (2006.01) | |
| *D06P 5/30* | (2006.01) | |
| *D06M 101/20* | (2006.01) | |
| *D06M 101/32* | (2006.01) | |
| *D06M 101/34* | (2006.01) | |

(52) U.S. Cl.
CPC .............. *A24D 3/10* (2013.01); *D01D 5/082* (2013.01); *D01D 5/36* (2013.01); *D01F 1/04* (2013.01); *D01F 1/06* (2013.01); *D01F 2/28* (2013.01); *D01G 15/46* (2013.01); *D06M 23/16* (2013.01); *D06P 5/00* (2013.01); *G01N 21/84* (2013.01); *G01N 33/365* (2013.01); *G06K 7/10* (2013.01); *G06K 7/1413* (2013.01); *G06K 9/62* (2013.01); *G06K 9/6217* (2013.01); *G06K 19/06046* (2013.01); *G06M 11/00* (2013.01); *G07D 7/12* (2013.01); *G07D 7/2033* (2013.01); *G09F 19/00* (2013.01); *D06M 2101/20* (2013.01); *D06M 2101/32* (2013.01); *D06M 2101/34* (2013.01); *D06P 5/30* (2013.01); *G01N 2021/8444* (2013.01); *G06K 2007/10504* (2013.01)

(58) Field of Classification Search
CPC .... A24D 3/10; A24D 3/063; G06K 19/06046; G06K 19/06; G06K 9/62; G06K 7/1413; G06K 9/6217; G06K 7/10; G06K 7/001; G06K 2007/10504; D01D 5/082; D01D 5/08; D01D 5/001; D01D 5/36; G09F 19/00; G09F 3/0297; G09F 3/00; G06M 11/00; G07D 7/12; G07D 7/2033; D01G 15/46; D01F 1/04; D01F 2/28; D01F 1/06; D06M 23/16; D06P 5/00; D06P 5/30

See application file for complete search history.

(56) References Cited

U.S. PATENT DOCUMENTS

| | | | |
|---|---|---|---|
| 4,280,925 A * | 7/1981 | Kiefer | B01J 20/28023 210/679 |
| 4,390,452 A | 6/1983 | Stevens | |
| 4,838,642 A | 6/1989 | De Jong et al. | |
| 5,744,000 A | 4/1998 | Athey et al. | |
| 6,036,885 A * | 3/2000 | Krutak, Sr. | C08B 1/003 106/170.1 |
| 6,607,813 B2 | 8/2003 | Washburn et al. | |
| 6,948,068 B2 | 9/2005 | Lawandy et al. | |
| 7,162,286 B2 | 1/2007 | Knoll et al. | |
| 7,163,744 B2 | 1/2007 | Nightingale et al. | |
| RE39,490 E | 2/2007 | Cote et al. | |
| 7,546,048 B2 | 6/2009 | Schwartz et al. | |
| 7,684,652 B2 | 3/2010 | Zorab et al. | |
| 7,995,196 B1 * | 8/2011 | Fraser | G06K 9/00577 356/71 |
| 8,158,253 B2 | 4/2012 | Spinks | |
| 8,171,567 B1 * | 5/2012 | Fraser | G06T 1/0021 713/176 |
| 8,409,705 B2 | 4/2013 | Spinks | |
| 8,748,079 B2 | 6/2014 | True | |
| 8,851,384 B2 | 10/2014 | Iwamoto | |
| 8,862,264 B2 | 10/2014 | Phan et al. | |
| 8,900,414 B2 | 12/2014 | Kaser | |
| 9,320,994 B2 | 4/2016 | McLeod et al. | |
| 2001/0037455 A1 | 11/2001 | Lawandy et al. | |
| 2002/0067603 A1* | 6/2002 | Driscoll | D04C 3/48 362/5 |
| 2003/0006324 A1 | 1/2003 | Pettigrew et al. | |
| 2003/0058990 A1 | 3/2003 | Kaiser et al. | |
| 2004/0034214 A1 | 2/2004 | Nightingale et al. | |
| 2005/0172977 A1* | 8/2005 | Jadot | A24C 5/005 131/365 |
| 2005/0227068 A1* | 10/2005 | Dugan | D01D 5/36 428/364 |
| 2007/0098974 A1* | 5/2007 | Nightingale | G06K 19/06046 428/292.1 |
| 2008/0216255 A1* | 9/2008 | Poovey | D02G 3/40 8/543 |
| 2010/0108754 A1* | 5/2010 | Kahn | D05C 11/00 235/375 |
| 2010/0239642 A1 | 9/2010 | Campbell et al. | |

FOREIGN PATENT DOCUMENTS

| | | |
|---|---|---|
| RU | 2080428 C1 | 5/1997 |
| WO | 9509947 A1 | 4/1995 |
| WO | 2011073442 A1 | 6/2011 |
| WO | 2013089688 A1 | 6/2013 |

OTHER PUBLICATIONS

Huang, Chaobo, et al.; "Digitally Encoded Nanoscopic Polymeric Fibers Prepared by Electrospinning"; Polymer Preprints, vol. 50, Issue 1; p. 92; 2009.

Huang, C. et al.; "Unbreakable Codes in Electrospun Fibers: Digitally Encoded Polymers to Stop Medicine Counterfeiting"; Advanced Materials, vol. 22, Issue 24; pp. 2657-2668; May 5, 2010.

McBride, Murdoch; "Tobacco's Illicit Trade—How Legislation, Enforcement and Public Awareness are Key to Tackling Illicit Trade, Part I—Overview"; Tobacco International; pp. 17-27; Dec. 2013.

Notification of Transmittal of the International Search Report and the Written Opinion of the International Searching Authority, or the Declaration dated Sep. 30, 2015 received in International Application No. PCT/US2015/037637.

Office Communication notification date Nov. 10, 2015 received in co-pending U. S. Appl. No. 14/748,745.

(56) References Cited

OTHER PUBLICATIONS http://www.gtin.info/barcode-101, cited on Notice of References Cited and uploaded to U.S. Appl. No. 14/748,865.

* cited by examiner

Schematic of concurrent branding and acetate tow productions

| Code | ⦀    | |
|---|---|
| Drop Size | Normal |
| Pixels | 9 |
| Delay | 10 |
| Width | 55 |
| Gap | 0 |
| Height | 150 |
| Orientation | Upside Down |

Figure 2

ID Technology® Ci3300 settings for branded fiber production

Stitched image of an encoded nylon fiber extracted from a filter rod

Stitched image of an encoded polyester thread extracted from a crimped acetate tow band An image of an acrylic monofilament fiber engraved using a MACSA carbon dioxide laser.

FIBERS WITH SURFACE MARKINGS USED FOR CODING

CROSS REFERENCES TO RELATED APPLICATIONS

This application is a Divisional application of U.S. Non-Provisional application Ser. No. 14/748,865 filed on Jun. 24, 2015 which claims priority under 35 U.S.C. 119(e) to U.S. Provisional Application Ser. No. 62/018,182, filed Jun. 27, 2014, U.S. Provisional Application Ser. No. 62/105,011, filed Jan. 19, 2015, and U.S. Provisional Application Ser. No. 62/164,135, filed May 20, 2015, each of which is incorporated herein by reference in its entirety.

TECHNICAL FIELD

This present disclosure relates to fibers, a fiber band, or a yarn containing branded fibers. The branded fibers can exhibit a repeated pattern of surface markings. The repeated pattern of surface markings can correlate to supply chain information of the fiber band or yarn. The present disclosure also relates to the method for making and characterizing the fiber band or yarn containing the branded fibers. Characterizing of the fiber band or yarn can include isolating the branded fibers, decoding the repeated pattern of surface markings, and correlating the repeated pattern of surface markings to supply chain information. The supply chain information can be used to track the fiber band or yarn from manufacturing through intermediaries, conversion to final product, and/or the consumer.

BACKGROUND

Many industries have a need to mark, tag, or identify products that allows for the tracking and tracing of products through the supply chain. One of the primary purposes for such track and trace systems is the combating of illicit trade such as counterfeiting and black market sales.

Anti-counterfeiting measures (ACMs) can be regarded as three different types: Type I (Overt), Type I (Covert) and Type III (Forensic). Type I ACMs are features incorporated into an article that are readily identified and observable to the naked eye. Examples include watermarks, color shifting inks, colored fibers, bands, or strips incorporated into the article, and holograms. Type II ACMs are features that are incorporated into the article that require some form of instrument to identify the feature in the field. The instruments required are generally those that are readily available and transportable. Some examples include the incorporation of very small text (requiring the use of a magnifying glass), UV responsive inks or threads (requiring illumination with a UV light), and barcodes or RFID tags (requiring a specialized reader). Type III ACMs are hidden attributes that require specialized laboratory equipment to identify. Some Type II examples include nano-text, micro-taggants, DNA inks, and chemical additives.

As stated above, there are many widely-used packaging and labelling taggants and anti-counterfeiting measures (ACMs) in many industries, but these more overt solutions are often susceptible to countermeasures such as destruction, modification, duplication, repackaging, or relabeling. Altering the physical features of the raw materials of a product can provide a more covert solution that is much more difficult to evade. These taggants may be used to track the fibers through the supply chain. The taggants may change the physical properties of the fibers, yarn fiber bands, and/or derivative articles in a manner that is difficult to copy or alter but is detectable using image analysis and/or other mechanical methods.

There is a need to manufacture, test, and track fibers in fiber bands or yarns and their derivative articles across a wide spectrum of industries. The ability to identify the source of a fiber band, yarn and/or an article comprising the fiber band or yarn can be achieved by embedding some form of a code in the fiber(s) during the manufacturing process that can then be later identified, retrieved, and used to identify the fiber band and/or the article.

Identification tags can be incorporated into the fibers, fiber band, or yarn that can denote, for example, manufacturer, manufacture site, customer, and ship-to location among other supply chain information that might be useful for the track and trace of the fiber band, yarn and/or article.

The disclosed exemplary embodiments can be used, for example, to combat the continuing and growing illicit-trade problem of tobacco products, particularly cigarettes. It has been estimated that 10-12% of all cigarette sales are illicit, either counterfeit copies or sales that avoid paying excise taxes on the cigarettes (Tobacco International, "Tackling Illicit Trade, Pt. I" December 2013). To combat this illicit trade requires a global effort consisting of manufacturers, distributors, regulators, and customs/law enforcement, as well as retailers who sell the cigarettes to consumers. There is a need to be able to track and ultimately trace components used in the construction of a cigarette. For example, the ability to track part of the supply chain path of acetate tow contained in the filter of a black market cigarette may give helpful information on the source of these illicit cigarettes.

Manufacturers of acetate tow typically assign a bale identifier (e.g., number) to each bale of acetate tow produced. Upon assignment, the bale number is associated with supply chain components such as manufacturer, manufacturing site, manufacturing line, production run, and production date. As the bale of acetate tow moves through the supply chain, additional supply chain components such as, for example, customer and ship-to location can be associated with the bale number. In other words, acetate tow manufacturers have systems in place to track and trace some of the supply chain components for bales of acetate tow. Currently, however, an equivalent of a bale number is not encoded in the acetate tow band itself. Therefore, once the label is removed from a bale of acetate tow or the acetate tow band is converted into a filter rod or cigarette filter, the supply chain information is lost.

There is a need for a traceable acetate tow that is readily manufactured, does not impact the performance of a cigarette filter, and is detectable, not only in an acetate tow band, but also in a single or a set of cigarettes/cigarette filters. There is a need for a traceable acetate tow that is readily accepted by cigarette manufacturers and consumers, such as an acetate tow that does not require adding chemicals which may impact taste and/or require regulatory approval. There is a need for traceable acetate tow that does not impact the pressure drop and yield of a cigarette filter. There is a need for traceable acetate tow that maintains its traceability when bloomed, plasticized, and formed into a filter.

There is a need for traceable acetate tow that contains supply chain information including a manufacturer, the customer, or the ship-to location such that the information can be decoded from a single or a set of cigarettes. There is a further need for traceable acetate tow with supply chain information at the level of the acetate tow bale in order to implement a traceable acetate tow system with minimal supply chain costs and complexities.

BRIEF SUMMARY

The embodiments disclose fibers comprising standard fibers one or more identification fibers. Each of the identification fibers exhibits at least one distinct feature. The identification fibers comprise one or more branded fibers. The branded fibers exhibit the distinct features comprising one or more taggant surface markings. The taggant surface markings form a repeated pattern along a length of the branded fibers. The taggant surface markings and the repeated pattern are representative of at least one supply chain component of the standard fibers.

Additional disclosed embodiments include an acetate tow band comprising fibers. The fibers comprise one or more identification fibers and standard fibers and the standard fibers comprise cellulose acetate. Each of the identification fibers exhibits at least one distinct feature. The identification fibers comprise one or more branded fibers. The branded fibers exhibit the distinct features comprising one or more taggant surface markings. The taggant surface markings form a repeated pattern along a length of the branded fibers. The taggant surface markings and the repeated pattern are representative of at least one supply chain component of the acetate tow band.

Further embodiments encompass methods of making an acetate tow band comprising fibers. The fibers comprise standard fibers and identification fibers and the standard fibers comprise cellulose acetate. The method comprises: (a) obtaining the identification fibers; (b) producing the standard fibers on a first fiber production process; and (c) combining the identification fibers and the standard fibers into the acetate tow band. Each of the identification fibers exhibits at least one distinct feature. The identification fibers comprise one or more branded fibers. The branded fibers exhibit the distinct features comprising one or more taggant surface markings. The taggant surface markings form a repeated pattern along a length of the branded fibers. The taggant surface markings and the repeated pattern are representative of at least one supply chain component of the acetate tow band.

Yet additional embodiments encompass methods of characterizing a fiber sample. The fiber sample comprises fibers and the fibers comprise standard fibers and identification fibers. Each of the identification fibers exhibits at least one distinct feature. The identification fibers comprise one or more branded fibers. The branded fibers exhibit the distinct features comprising one or more taggant surface markings. The taggant surface markings form a repeated pattern along a length of the branded fibers. The method comprises (1) optionally separating the branded fibers from the fiber sample; (2) applying imaging technology to the branded fibers; (3) determining the repeated pattern of the taggant surface markings. The taggant surface markings and the repeated pattern are representative of at least one supply chain component of the fiber sample.

BRIEF DESCRIPTION OF THE DRAWINGS

FIG. 2 illustrates the printer settings for Example 1.

DETAILED DESCRIPTION

Figure 1:
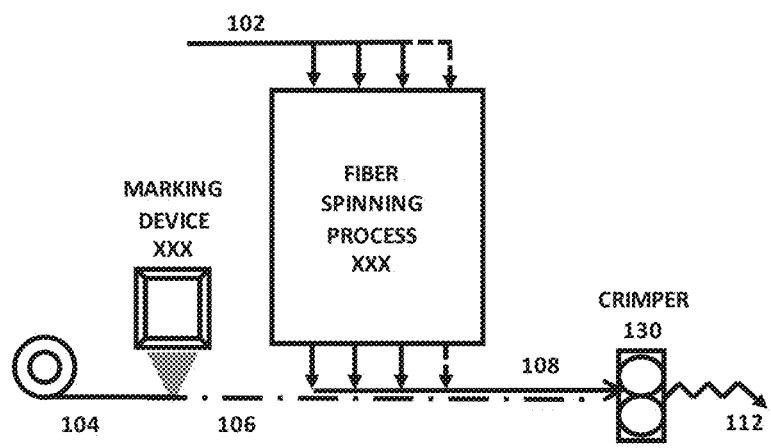
FIG. 1 shows a schematic process flow diagram of a non-limiting embodiment of branding fibers while coproducing acetate tow fibers and combining them into an acetate tow band.

The embodiments disclose fibers comprising one or more identification fibers. Each of the identification fibers exhibits at least one distinct feature. The identification fibers comprise one or more branded fibers. The branded fibers exhibit the distinct features comprising one or more taggant surface markings. The taggant surface markings form a repeated pattern along a length of the branded fibers. The taggant surface markings and the repeated pattern are representative of at least one supply chain component of the standard fibers.

Unless otherwise indicated, all numbers expressing quantities of ingredients, properties such as molecular weight, reaction conditions, and so forth used in the specification and claims are to be understood as being modified in all instances by the term "about."

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "fibers", as used herein, refers to thin flexible threadlike objects. Fibers can be natural fibers or man-made. The term "polymer", as used herein refers to the base material from which the fibers are made. Non-limiting examples of polymers include acrylic, modacrylic, aramid, nylon, polyester, polypropylene, rayon, polyacrylonitrile, polyethylene, PTFE, and cellulose acetate. The term "filament", as used herein, refers to a single fiber. The term "fiber band", as used herein, refers to multiple fibers placed adjacent to each other along their lengths such that the fibers remain untwisted or entangled and form a substantially rectangular cross section with a high width-to-depth ratio. Fiber bands are often formed to allow for effective crimping of the fibers and can be cut into a staple or processed as a continuous band, depending on the end use. Fiber bands are typically not woven or knitted into a fabric article unless first converted into staple to form a thread. Fibers can also be in the form of yarns. The term "yarn, as used herein, refers to multiple fibers placed adjacent to each other along their lengths, often twisted or entangled together to improve fiber cohesiveness and performance, and typically forming a substantially rounded cross section. Yarn can be processed as continuous strands or cut into smaller lengths, depending on the end use.

Fibers can be identification fibers and/or standard fibers. The term "standard fibers", as used herein, refers to fibers which are manufactured for the primary purpose and use in producing articles. Standard fibers have not been purposefully manipulated to comprise distinct features used to identify and track the standard fibers, yarn, a fiber band, and/or an article comprising standard fibers. The term "identification fibers", as used herein, refers to the fibers having distinct features such that the identification fibers can be used to identify and track the standard fibers, yarn, a fiber band, and/or an article comprising the standard fibers and the identification fibers.

The term "distinct features", as used herein, refers to variances among fibers that can be identified using imaging technology. Non-limiting examples of distinct features include cross-section shapes, cross-section sizes, optical properties, and surface markings. The term "combination of distinct features", as used herein, refers to the two or more distinct features exhibited by an identification fiber.

The term, "optical properties", as used herein, refers to electromagnetic radiation responses observed when the fibers are exposed to a specific electromagnetic radiation sources. The term includes color which can be observed with the human eye as well as with an instrument such as one capable of identifying a spectrophotometric signature. Non-limiting examples of electromagnetic radiation include x-ray, ultraviolet, visible light, infrared, and so-called "T-ray" (terahertz frequencies). The term "taggant optical properties", as used herein refers to a collection of known optical properties used by one or more manufacturer in a system for determining fibers, fiber band, and/or yarn supply chain information.

The term, "surface markings", as used herein, refers to variances in the fibers produced by physically altering the fiber surface. Non-limiting examples include engraving the fiber, morphological modification, printing on the fiber surface, and chemically producing a pattern of optical properties. The term "taggant surface markings", as used herein refers to a collection of known surface markings used by one or more manufacturer in a system for determining chain information.

The term "alphanumeric code", as used herein, refers to information that is represented using the characters or letterings belonging to a common alphabetic and numerical system or language, including special characters such as punctuation marks and including any script or printing style for that language. Non-limiting examples include the Latin alphabet, Roman numerals, and Arabic numbering.

The term "digital code", as used herein, refers to information that is represented using a string of discrete, discontinuous values. Non-limiting examples include binary coding systems, Morse Code, bar coding systems (including 1-D linear and 2-D matrix), The term "analog code", as used herein, refers to information that is represented by modulating a continuously variable physical quantity such as spatial position, a dimension, or a magnitude.

The term an "ideographic code", as used herein, refers to information that is represented by a graphic symbol or pictograph, independent of any particular language or alphanumeric system.

The term "metadata", as used herein, refers to a portion or multiple portions of the pattern that represents a code that contains information about the remaining code within the pattern. Non-limiting examples of this information includes the format, read-start position, read-end position, read direction of any code the pattern represents. The metadata could also include information that represents the manufacturer of the fiber. The metadata may use the same or similar coding system as that used for the remaining portion of the pattern or it may use a different coding system to easily differentiate it from the remaining portion of the pattern.

The term "read-start position," as used herein, refers to the position where a code or a portion of a code begins.

The term "read-end position," as used herein, refers to the position where a code or a portion of a code ends.

The term "read-direction," as used herein, refers to the linear direction a particular portion of the code must be read to reliably decode the information.

The term "the repeated pattern is essentially one-dimensional", as used herein, refers to a pattern where the useful information associated with the pattern is along one direction or can be determined by observing the variation along a single line through the pattern.

The term "engraving", as used herein, refers to the removal of material from the fiber surface or the creation of raised or recessed areas on the fiber surface such that the resulting discontinuities in the fiber surface can be detected optically or by other analytical means. Engraving can be performed by contact equipment, such as equipment that uses abrasive surfaces, blades, or embossers, or by noncontact equipment, such as lasers or other high energy radiation sources.

The term "laser engraving", as used herein, refers the use of a laser to engrave the surface of a fiber.

The term "morphological modification", as used herein, refers to a change in the physical form or condition of the fiber or the fiber surface such that the change can be observed optically, either manually or through magnification, or through other analytical techniques. Non-limiting examples of morphological modification include changes to texture, roughness, opacity, crystallinity, density, or degree of polymer orientation. Morphology modification can be performed by contact equipment, such as equipment that uses abrasive surfaces, or by noncontact equipment such as lasers or other high energy radiation sources.

The term "vary along the length", as used herein, refers to the use of various levels and/or patterns of one or more surface markings along the length of an identification fiber. The term, "repeating patterns", as used herein, refers to a repeated identical sequence of surface makings along the length of the identification fibers. Each repeated pattern is representative of the same code of the same information.

The term "essentially not susceptible to solvent bonding", as used herein, refers to a condition such that the fibers are not, under the normal processing conditions of the fibers or the articles made from the fibers, sufficiently soluble in a bonding agent to allow for permanent bonding at the contacting points of two or more fibers when the bonding agent is present at the contact points.

The term "essentially insoluble in a solvent", as used herein, refers to a condition such that the fibers are not sufficiently soluble in a solvent such that when exposed to that solvent under a certain set of conditions, the fiber and any surface markings remain detectable.

The term "dissolved portion of the fiber sample", as used herein, refers to a solution containing the dissolved standard fibers and the dissolving solvent to the exclusion of any non-soluble identification fibers in the sample.

The term, "cellulose acetate", as used herein, refers to an acetate ester of cellulose wherein the hydrogen in the hydroxyl groups of the cellulose glucose unit is replaced by acetyl groups through an acetylation reaction. In some embodiments, suitable cellulose acetates may have a degree of substitution less than about 3 acetyl groups per glucose unit, preferably in the range of 2.2 to about 2.8, and most preferably in the range of 2.4 to 2.7.

The terms, "cellulose acetate tow", "acetate tow", or "acetate tow band" as used herein, refers to a continuous, crimped fiber band comprising of cellulose acetate fibers.

The term, "article", as used herein, refers to a unit produced from standard fibers, yarn, and/or a fiber band, including other components and additives needed to meet the functional requirements of the intended use. Non-limiting examples include fabrics and other textile products, non-wovens, absorbent products, filters, filter rods, cigarette filters and liquid storage reservoirs. The term "article comprising fibers, yarn and/or fiber bands", as used herein, refers to the article comprising the fibers, yarn and/or fiber bands with a recognition that, in some embodiments, significant physical changes can occur to the fibers, yarn and/or fiber band, when it is used to make an article.

The term, "filter", as used herein refers to a semi-permeable fibrous material. Non-limiting examples of filters include a filter rod, and items made from a filter rod such as a cigarette filter. The term "filter rod", as used herein, refers to a rod-like article, of any cross-sectional shape, produced from a fiber band and other components or additives, which can be subsequently used as a whole unit, or cut into lengths to form multiple units, for filtration of a vapor stream. Filter rods can be used to filter tobacco products, for example, traditional cigarette filters and/or other applications for other tobacco products including heat-not-burn products. Filter rods can also be used for new products comprising tobacco and other ingredients such as, for example, other plants or plant derivatives. Filter rods can be used to filter other plants and plant derivatives, with or without tobacco present. Additionally filter rods can be used to filter any vapor stream used to deliver an active ingredient such as in e-cigarette.

The term, "cigarette filter", as used herein, refers to a component of the cigarette or other smoking device which removes or decreases one or more elements from a smoke stream. The term cigarette filter is intended to encompass the filter on any smoking device including the non-limiting examples of a cigarette, a cigarette holder, a cigar, a cigar holder, a pipe, a water pipe, a hookah, an electronic smoking device, a roll-your-own cigarette, a roll-your-own cigar, and a paper.

The term, "supply chain information" as used herein, refers to information regarding the production of the standard fibers, yarn, and/or fiber band and information regarding the distribution of the standard fibers, yarn, and/or fiber band after its production. Supply chain information includes "supply chain components" such as, for example, manufacturer, manufacture site, manufacture line, production run, production date, a package, bale, customer, customer ship-to location, warehouses, freight carrier, and/or shipment paths or routes. Supply chain components can apply to fibers, yarn, fiber bands, and/or articles.

The term, "manufacturer", as used herein, refers to the entity that produces the standard fibers, yarn and/or fiber band.

The term "manufacture site", as used herein, refers to the geographic location or locations of the manufacturer, designated by any level of specificity including full address, continent, country, state, province, county, or city.

The term "manufacture line", as used herein, refers to specific process equipment or set of equipment used by the manufacturer to produce the standard fibers, yarn, and/or fiber band.

The term "production run", as used herein, refers to a group or set of similar or related goods that are produced by using a particular set of manufacturing procedures, processes, or conditions and/or product specifications.

The term "customer", as used herein, refers to an entity to which the fibers, fiber band, and/or yarn is sold and shipped for further processing into an intermediate article or a finished product article; or an entity that purchases the fibers, yarn and/or fiber band for resale.

The term, "ship-to location", as used herein, refers to the geographic location of the customer designated for delivery of the fibers, yarn and/or, fiber band by any level of specificity including full address, continent, country, state, province, county, or city.

The term, "bale" as used herein, refers to a packaged unit of fiber bands, typically of a cubical shape, compressed to a high density, and wrapped, contained, and protected by packaging material.

The term, "warehouse" as used herein, refers to the geographical location of the warehouse designated for delivery of the fibers, yarn and/or, fiber band by any level of specificity including full address, continent, country, state, province, country, or city.

The term, "correlating", as used herein refers to establishing the relationship between two or more pieces of information.

The term, "manufacturer specific taggants", as used herein, refers to the particular taggants incorporated into fibers, yarn and/or, fiber band by a particular manufacturer. The term, "manufacturer specific taggant set" refers to the taggant cross-section shapes and/or taggant cross-section sizes associated with a particular manufacturer.

The term, "fibers are produced", "producing fibers", and "fiber production process", as used herein, refers to the process steps of spinning fibers up through the gathering of the fibers.

The term "concurrently to producing", as used herein, refers to process of surface marking identification fibers at the same time that the standard fibers are being produced, either prior to or after the identification fibers are combined with the standard fibers.

The term, "identification fibers are packaged", as used herein, refers to the process steps of transferring identification fibers from the spinning machine and packaging the identification fibers, for example, onto a spool or into a bale. The identification fibers would subsequently need to be removed from the package in order to be incorporated into fibers, yarns, fiber band, and/or article comprising the standard fibers.

The term "fiber sample", as used herein, refers to the item comprising fibers, in any physical form, being analyzed using imaging technology. The fiber sample can comprise a portion of a set of fibers, yarn, a fiber band, or an article which has been prepared for image analysis.

The terms, "imaging technology", and "image analysis techniques" as used herein, refer to the equipment and software used to detect and quantify differences in reflection, absorption, transmission, and emittance of electromagnetic radiation. Imaging technology encompasses both electromagnetic radiation level detection and automated shape and/or size recognition.

Fibers, a fiber band, and/or a yarn comprise individual fibers. The material from which the fibers are made is not particularly limiting. The fibers can comprise, for example, acrylic, modacrylic, aramid, nylon, polyester, polypropylene, rayon, or cellulose acetate. In one aspect, the fibers comprise cellulose acetates, cellulose triacetates, cellulose propionates, cellulose butyrates, cellulose acetate-propionates, cellulose acetate-butyrates, cellulose propionate-butyrates, cellulose acetate-phthalates, starch acetates, acrylonitriles, vinyl chlorides, vinyl esters, vinyl ethers, and the like, any derivative thereof, any copolymer thereof, and any combination thereof. In one aspect, the fibers comprise cellulose acetate. In one aspect, the fibers comprise natural fibers such as, for example, cotton, hemp, and/or silk.

In one aspect, the fibers, fiber band, or yarn comprises standard fibers and one or more identification fibers. Fibers are typically produced from a polymer. In one aspect, one or more of the identification fibers comprise the same polymer as the standard fibers. In another aspect, one or more of the identification fibers comprise a different polymer than the standard fibers band. In one aspect, the taggant surface markings and the repeated pattern are representative of a code of the fibers. In other aspects the fibers comprise identification fibers and standard fibers and the code is representative of at least one supply chain component of the fibers and/or standard fibers.

The size of the individual fibers is not particularly limiting. The size can be given in terms of effective diameter, and in one aspect, the effective diameter of the fibers range, for example, from 0.1 µm to 1000 µm, 1 µm to 500 µm, 1 µm to 100 µm, 1 µm to 30 µm, 10 µm to 1000 µm, 10 µm to 500 µm, 10 µm to 100 µm, 10 µm to 30 µm. In one aspect, the standard fibers comprise cellulose acetate for which size is often given in terms of denier per filament (dpf) which is defined as the weight, in grams, of a single filament 9000 meters in length. In one aspect, the size of the fibers ranges from 0.5 to 1000 dpf; 0.5 to 500 dpf; 0.5 to 100; 0.5 to 5 dpf; 0.5 to 30 dpf; 0.5 to 10 dpf; 1 to 1000 dpf; 1 to 500 dpf; 1 to 100; 1 to 5 dpf; 1 to 30 dpf; 1 to 10 dpf. In one aspect, the dpf of the fibers ranges from, for example, 1 to 30 dpf, 1 to 20 dpf, 1 to 10 dpf, 2 to 30 dpf, 2 to 20 dpf, or 2 to 10 dpf.

The number of fibers making up a fiber band is not particularly limiting. In one aspect, the number of fibers in a fiber band can range from 10 to 50,000. In other non-limiting examples, the number of fibers in a fiber band ranges from 10 to 40,000; 10 to 30,000; 10 to 20,000; 10 to 10,000; 10 to 1000; 100 to 50,000; 100 to 40,000; 100 to 30,000; 100 to 20,000; 100 to 10,000; 100 to 1000; 200 to 50,000; 200 to 40,000; 200 to 30,000; 200 to 20,000; 200 to 10,000; 200 to 1000; 1000 to 50,000; 1000 to 40,000; 1000 to 30,000; 1000 to 20,000; 1000 to 10,000; 5000 to 50,000; 5000 to 40,000; 5000 to 30,000; 5000 to 20,000; 5000 to 10,000; 10,000 to 50,000; 10,000 to 40,000; 10,000 to 30,000; or 10,000 to 20,000.

Identification fibers can comprise one or more branded fibers. The branded fibers exhibit one or more taggant surface markings wherein the taggant surface markings form a repeated pattern along the length of the branded fibers. In one aspect, branded fibers can be a monofilament wherein the taggant surface markings form a repeated pattern along the length of the monofilament. In other aspects, the branded fibers can be a thread or yarn wherein the taggant surface markings form a repeated pattern along the length of the thread or yarn. The repeated pattern can be representative of a code which can correlate to information such as, for example, supply chain information.

In some aspects, the repeated pattern comprises an alphanumeric code, a digital code, an analog code, or an ideographic code. In some aspects, the repeated pattern comprises an alphanumeric code or a digital code. In some aspects, the repeated pattern comprises a digital code.

The repeated pattern along the length of the branded fibers may include metadata. The metadata can be useful in reading the pattern on the branded fibers. The metadata can be especially useful if the length of the branded fiber incorporated into an article is approximately the same size or smaller than the length of the repeated pattern. In one aspect, the metadata comprises read-start position, read-end position, read direction, or the spacing of the digits within the code.

The digital code of the repeated pattern is not particularly limited. In some aspects the pattern is in the form of a bar code, either a 1-D linear or 2-D matrix type code. In some aspects the pattern could be a visual representation of a Morse code. In some aspects the digital code comprises a binary code. In one aspect, the repeated pattern is essentially one-dimensional.

In one aspect, the digital code is a binary coding system, the two conditions or characters of each binary digit can be the presence or absence of a surface marking in a digit or location. In an alternative aspect, the two conditions could be one of two different surface markings in a digit In some aspects the digital code could be a binary representation of a place-value system of base x, where x is a power of 2 (or a binary). In one aspect, for example, when large number of combinations or integer values is to be coded, a hexadecimal (base 16) numbering system can be used to provide a notation that is more compact than a simple binary string. In a non-limiting illustration of such a hexadecimal system, 4 binary digits could make up each digit of the hexadecimal code, providing the 16 combinations or conditions for each of the hexadecimal digits. Base-x numbering systems can also be represented by x-number of unique surface markings in any digit or spacial location. In a non-limiting example, 5 different color dots can form the basis of a base-5 numbering system.

Multiple numbering or coding systems may be used in a single string of encoded information. In some aspects, the repeated pattern can contain a portion of binary coding with the sequence used to represent the manufacturer of the fiber or article and another portion of the pattern that is a binary representation of a hexadecimal system used to represent unique bale numbers of the manufacturer.

One skilled in the art recognizes that the selection of the number of digits for the binary code depends upon the complexity of information being captured and the space available for the taggant surface markings. In one aspect, the number of digits in the binary code ranges from 2 to 500. In other non-limiting examples, the number of digits in the binary code ranges from 4 to 100, 10 to 100, 20 to 100, 4 to 50, 10 to 50, or 20 to 50.

One skilled in the art also recognizes that the length of the repeated pattern on the fibers may be influenced by the length the fiber incorporated in typical articles. In one aspect, the length of the repeated pattern ranges from 2 mm to 500 mm. In other non-limiting examples, the length of the repeated pattern ranges from 2 to 200 mm, 2 to 30 mm, 10 to 200 mm, or 10 to 30 mm.

The manner in which the repeated pattern appears on the branded fiber is not particularly limited, so long as the pattern is recognizable. Non-limiting examples of how the repeated pattern is incorporated on the branded fiber include printing, engraving, morphological modifications of the fiber, or chemically producing a pattern of optical properties.

In some aspects, the fibers further comprise standard fibers. In some aspects, the branded fibers are readily separated from the standard fibers by either physical or chemical means. In order to facilitate the separation of the branded fibers, the branded fiber can comprise a different polymer than the standard fibers. In some aspects, the branded fibers are essentially insoluble in a solvent, wherein the standard fibers are soluble in that same solvent. In some aspects the branded fibers are essentially insoluble in acetone or methylene chloride. In some aspects, the branded fibers are essentially not susceptible to cold-solvent bonding with triacetin or any other solvent or plasticizer that is used to form an article by solvent-bonding the standard fibers. In some aspects, the branded fibers comprise acrylic, modacrylic, aramid, nylon, polyester, polypropylene, rayon, polyacrylonitrile, polyethylene, cellulose triacetate, or PTFE.

An article can comprise the fibers, yarn, and/or a fiber band. The article is not particularly limited. Non-limiting examples of articles comprising the fibers or the fiber band include fabrics and other textile products, non-wovens, absorbent products, filters, filter rods, cigarette filters, liquid storage reservoirs, paper and/or currency. In one aspect, the article comprises a filter rod. In another aspect, the article comprises a cigarette filter. Additional non-limited examples of articles include medical items such as medical tape, bandages, or cloth, wicking devices used for vapor delivery, and pharmaceutical products including packaging.

In one aspect, the fibers, yarn, fiber band, and/or article have determinable supply chain information. The supply chain information can include manufacturer, manufacture site, manufacturing line, production run, production date, package, bale, warehouse, customer, and/or ship-to location.

In one aspect, the supply chain information comprises supply chain components. In one aspect, at least one supply chain component comprises a manufacturer of the standard fibers, a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a yarn or fiber band comprising the standard fibers, a manufacturing site of the yarn or fiber band, a manufacturing line of the yarn or fiber band, a production run of the yarn or fiber band, a production date of the yarn or fiber band, a package of the yarn or fiber band, a warehouse of the yarn or fiber band, a customer of the yarn or fiber band, a ship-to location of the yarn or fiber band, a manufacturer of an article comprising the standard fibers, a manufacture site of the article, a manufacturing line of the article, a production run of the article, a production date of the article, a package of the article, a warehouse of the article, a customer of the article, or a ship-to location of the article.

In another aspect at least one supply chain component comprises the manufacturer of the yarn or fiber band. In one aspect, the supply chain component comprises the manufacture site of the yarn or fiber band. In one aspect the supply chain component comprises the manufacturing line of the yarn or fiber band. The manufacturing line of the yarn or fiber band is the manufacturing line on which the yarn or fiber band was produced. In one aspect, the supply chain component comprises the production run of the yarn or fiber band. The production run of the yarn or fiber band is the production run within which the yarn or fiber band was produced. In one aspect, the supply chain component comprises the production date of the yarn or fiber band. The production date of the yarn or fiber band is the production date on which the yarn or fiber band was produced. In one aspect, the supply chain component comprises the package of the yarn or bale of the fiber band. In one aspect, the supply chain component comprises the warehouse of the yarn or fiber band. The warehouse of the yarn or fiber band is the warehouse to which the manufacturer plans to send or has sent the fiber band. In one aspect, the supply chain component comprises the customer of the yarn or fiber band. The customer of the yarn or fiber band is the customer to whom the manufacturer plans to send or has sent the yarn or fiber band. In one aspect, the supply chain component comprises the ship-to location of the yarn or fiber band. The ship-to location of the yarn or fiber band is the specific geographic location to which the manufacturer plans to send or has sent the yarn or fiber band.

The following is a non-limiting illustration of a possible binary coding system that demonstrates the ability to create many different code combinations on the branded fiber contained within a typical cigarette filter.

In the work of Example 1 below, the length of the crimped monofilament fiber or thread within a typical 21 mm length cigarette filter was shown to be approximately 25.2 mm. In addition, a spacing of printed marks of 0.5 mm was shown to be readily achievable using the printer of the example. Such a spacing applied to a 25 mm fiber length would allow up to 50 bits or digits to be encoded on the branded fiber within each cigarette filter. Each bit would contain binary-type (0 or 1) information corresponding to existence or non-existence of a printed mark within the space.

In order to eliminate translational and rotational decoding errors in decoding, metadata in the form of a header may be desired with the coded sequence. The header could provide read start and read direction information. Such a header would allow for the reliable decoding of any one cigarette filter with a coding frequency as low as one code per cigarette filter. The header could take the form of a binary sequence designed such that it could not be confused with the characters of the code itself. For example, for a hexadecimal system in binary notation, the 10 bit sequence 0011111010 might be used.

Of the remaining 40 bits of the 50 bits available of this example, 39 bits could be used to express 8 hexadecimal characters in binary (8×4 digits, plus spaces between each 4-digit character) to encode a sequence that would take the form (####_####_####_####_####_## ##_####_####). With this format, 4,294,967,296 unique codes could be generated or, by using standard binary numbering, the numbers 0 to 4,294,967,295 could be generated. These codes or numbers could be correlated to supply chain information, such as bale numbers.

To further illustrate the example, the number 4,294,967,295 would be converted to its hexadecimal binary form 11111110110111111101111011101111101111. The complete code, including the header, would be 0011111010111011101110111011101110111101111101111.

The current world-wide demand for acetate tow for cigarette filtration is approximately 700,000,000 kg per year.

Assuming an average bale weight of 500 kg, the total number of bales produced in one year is approximately 1.4M. The implementation of a printed coding system of this example could therefore encode supply chain information at the bale level for over 3000 years' worth of production. In some aspects, fewer digits are used in each code and typical cigarette filters contain more than one repeat pattern of taggant surface markings.

Additional disclosed embodiments include an acetate tow band comprising fibers. The fibers comprise one or more identification fibers and standard fibers and the standard fibers comprise cellulose acetate. Each of the identification fibers exhibits at least one distinct feature. The identification fibers comprise one or more branded fibers. The branded fibers exhibit the distinct features comprising one or more taggant surface markings. The taggant surface markings form a repeated pattern along a length of the branded fibers. The taggant surface markings and the repeated pattern are representative of at least one supply chain component of the acetate tow band.

Embodiments of an acetate tow band encompass acetate tow bands comprising fibers with any combination of attributes disclosed above. Specifically, the identification fiber composition, the sizes and numbers of fibers, the branded fibers, the surface markings, the repeated patterns, the length of the repeated patterns, the supply chain information, and the non-limiting coding/correlation systems apply to the acetate tow band.

In one aspect, the at least one supply chain component comprises a manufacturer of the acetate tow band, a manufacturing site of the acetate tow band, a manufacturing line of the acetate tow band, a production run of the acetate tow band, a production date of the acetate tow band, a bale of the acetate tow band, a warehouse of the acetate tow band, a customer of the acetate tow band, or a ship-to location of the acetate tow band. In one aspect, the at least one supply chain component comprises the manufacturer of the acetate tow band and the customer of the acetate tow band. In another aspect, the least one supply chain component comprises the manufacturer of the acetate tow band and the customer of the acetate tow band. In one aspect, the at least one supply chain component comprises the bale of the acetate tow band.

Further embodiments encompass methods of making an acetate tow band comprising fibers. The fibers comprise standard fibers and identification fibers and the standard fibers comprise cellulose acetate. The method comprises: (a) obtaining the identification fibers; (b) producing the standard fibers on a first fiber production process; and (c) combining the identification fibers and the standard fibers into the acetate tow band. Each of the identification fibers exhibits at least one distinct feature. The identification fibers comprise one or more branded fibers. The branded fibers exhibit the distinct features comprising one or more taggant surface markings. The taggant surface markings form a repeated pattern along a length of the branded fibers. The taggant surface markings and the repeated pattern are representative of at least one supply chain component of the acetate tow band.

Embodiments of a method of making an acetate tow band encompass acetate tow bands comprising fibers with any combination of attributes disclosed above. Specifically, the identification fiber composition, the sizes and numbers of fibers, the branded fibers, the surface markings, the repeated patterns, the length of the repeated patterns, the supply chain information, and the non-limiting coding/correlation systems apply to the method of making the acetate tow band. The supply chain attributes of embodiments of the acetate tow band described above also applied to the method of making the acetate tow band.

One skilled in the art recognizes that the embodiments of method of making an acetate tow band, apply generally to making a fiber band or yarn. The identification fibers can be combined with standard fibers into a yarn or fiber band. The method for making a yarn or fiber band encompasses making fibers, a fiber band, or yarn comprising the fibers with any combination of attributes disclosed above.

In one aspect, at least a portion of the standard fibers are produced on a fiber production process. In another aspect, standard fibers are received from a third party. Obtaining the identification fibers comprises at least one of (i) producing at least a portion of the identification fibers on the standard fibers' fiber production process, (ii) producing at least a portion of the identification fibers on a process distinct from the standard fibers' fiber production process, or (iii) receiving at least a portion of the identification fibers from a third party.

In one aspect, a portion of the identification fibers are coproduced with the standard fibers and a portion of the fibers making up a fiber band or yarn are spun and combined directly downstream of the fiber production process.

When and where the identification fibers are surface marked is not particularly limiting. If the identification and standard fibers are made concurrently on the same spinning equipment, the surface markings can be applied anywhere between the start of the spinning process when the fiber is first physically formed and prior to the packaging of the fibers. In some aspects, the marking can be performed prior to the identification fibers and standard fibers being combined or, at least, prior to subsequent processing of the combined fibers, such as prior to crimping. In some aspects, the branded fibers are produced separately from the standard fibers on a separate spinning process, the surface markings can be applied at any time prior to their combining with the standard fibers, including by a third party, or concurrent with their combining with the standard fibers. In some aspects, the marking can take place just prior to the combining or at any point before the packaging of the fibers.

Non-limiting examples of methods of surface marking the identification fibers include printing, engraving, morphological modification, and chemically producing a pattern of optical properties. In some aspects, the printing of the surface markings could be performed using a commercial high-speed printer, such as an ink-jet printer, or a custom printer designed for purpose. The printing can be performed with a single ink of one color or with multiple ink colors. In some aspects, engraving could be performed by contact equipment, such as equipment that uses abrasive surfaces, blades, or embossing rollers, or by noncontact equipment, such as lasers or other high energy radiation sources. In some aspects a morphology modification can be performed by contact equipment, such as equipment that uses abrasive surfaces, or by noncontact equipment such as lasers or other high energy radiation sources. One non-limiting example of such a morphology change is the use of an energy source to induce intermittent fast drying of the fiber during its formation resulting in variations in optical properties of the fiber, such as opacity, or variations in surface roughness.

In some aspects branded fibers are produced on a second fiber production process followed by applying the taggant surface markings in the repeated pattern. In some aspects, fibers are received from a third party. The taggant surface markings in the repeated pattern can be applied to the fibers to produce branded fibers any time before the branded fibers are combined with the standard fibers into an acetate tow band. The manner in which the taggant surface markings in the repeated pattern is applied to the branded fibers is not particularly limited. In some aspects the taggant surface markings in the repeated pattern are printed on the branded fibers concurrently to producing the standard fibers. In some aspects the taggant surface markings in the repeated pattern are laser engraved on the branded fibers concurrently to producing the standard fibers. In some aspects the concurrently produced branded fibers and the standard fibers are combined prior to crimping the acetate tow band.

Whether the identification fibers and standard fibers are made on the same or different equipment, the marking of the identification fibers concurrent with the production of (or the combining with) the standard fibers the can be advantageous as it reduces complexity of managing and inventorying of pre-marked fibers and routing those branded fibers to designated production lines at the right time to ensure proper coding of the fiber product. In contrast, concurrent marking of the identification fibers can be readily controlled by standard computer systems (e.g., a PLC or a DCS), with the coding changed automatically and essentially instantaneously to code the desired supply chain information for the fiber being produced.

In another aspect, the identification fibers are produced and packaged separately from the standard fibers and the identification fibers are combined with the standard fibers to produce a fiber band or yarn. The standard fibers may also have been packaged before combining with the identification fibers, or the identification fibers may be combined with the standard fibers before packaging of the fiber band or yarn.

The spinning process used for producing the fibers is not particularly limited. In one aspect, the fibers are produced using dry spinning, solution spinning, melt spinning, electro spinning, gel spinning, multicomponent spinning, melt blowing, and/or solution blowing. In another aspect, the fibers are produced using dry spinning, solution spinning, melt spinning, electro spinning, gel spinning, and/or multicomponent spinning. In a further aspect, the standard fibers comprise cellulose acetate and are produced using dry spinning.

In some aspects the taggant surface markings in the repeated pattern are applied by process comprising engraving, printing, or morphological modification. In some aspects, the taggant surface markings in the repeated pattern are applied by process comprising printing the taggant surface markings in the repeated pattern on the branded fibers concurrently to producing the standard fibers and combining the branded fibers and the standard fibers before crimping the acetate tow band. In yet additional aspects, the taggant surface markings in the repeated pattern are applied by process comprising laser engraving the taggant surface markings in the repeated pattern on the branded fibers concurrently to producing the standard fibers and combining the branded fibers and the standard fibers before crimping the acetate tow band.

FIG. 1 shows a schematic process flow diagram of a non-limiting embodiment of branding fibers while coproducing acetate tow fibers and combining them into an acetate tow band. Acetate tow band 112 is produced in manufacturing environment 100. Cellulose acetate spinning solution 102 is fed to fiber spinning process 120 where it is fed to several spinning cabinets, each with several spinnerets (not shown). The fibers 108 exiting each spinning cabinet, often called ends, are gathered together to form a band which is fed into a crimper 130. Identification fiber 104 passes under marking device 110 which imparts surface markings in a repeated pattern to produce branded fiber 106. Non-limiting examples of marking device 110 include a printer and a laser. Branded fiber 106 and cellulose acetate fibers 108 are gathered together and fed to crimper 130 to produced crimped acetate tow band 112.

Yet additional embodiments encompass methods of characterizing a fiber sample. The fiber sample comprises fibers and the fibers comprise standard fibers and identification fibers. Each of the identification fibers exhibits at least one distinct feature. The identification fibers comprise one or more branded fibers. The branded fibers exhibit the distinct features comprising one or more taggant surface markings. The taggant surface markings form a repeated pattern along a length of the branded fibers. The method comprises applying imaging technology to the branded fibers and determining the repeated pattern of the taggant surface markings. The taggant surface markings and the repeated pattern are representative of at least one supply chain component of the fiber sample.

Yet additional embodiments encompass methods of characterizing a fiber sample. The fiber sample comprises fibers and the fibers comprise standard fibers and identification fibers. Each of the identification fibers exhibits at least one distinct feature. The identification fibers comprise one or more branded fibers. The branded fibers exhibit the distinct features comprising one or more taggant surface markings. The taggant surface markings form a repeated pattern along a length of the branded fibers. The method comprises (1) optionally separating the branded fibers from the fiber sample; (2) applying imaging technology to the branded fibers; (3) determining the repeated pattern of the taggant surface markings. The taggant surface markings and the repeated pattern are representative of at least one supply chain component of the fiber sample.

Embodiments of methods of characterizing a fiber sample encompass characterizing a fiber sample comprising fibers with any combination of attributes disclosed above. Specifically, the identification fiber composition, the sizes and numbers of fibers, the branded fibers, the surface markings, the repeated patterns, the length of the repeated patterns, the supply chain information, and the non-limiting coding/correlation systems apply to the method of characterizing a fiber sample.

The process of separating the branded fibers from the standard fibers of an article for the purpose of characterizing the branded fibers can depend on the nature of the article, the orientation, entanglement, and bonding of the fibers within the article, and the differences in the chemical composition of standard and branded fibers. In the case of a typical cigarette filter or similarly solvent-bonded fiber matts, in some aspects, the branded fibers are not susceptible to the solvent bonding agent used in the manufacture of the article, the branded fibers can be located (with or without magnification) and removed by hand or some other means to physically segregate the branded fibers from the rest of the fiber sample. In some aspects, the branded fibers have a solubility profile different from the standard fibers and the standard fibers can be dissolved away from the branded fibers with the use of the right combination of solvents and/or conditions. In some aspects, cigarette filters comprise cellulose acetate and the branded fibers comprise a polymer that is not soluble in acetone such that acetone can be used to dissolve away the standard fibers and segregate the branded fibers. In some aspects, separating the branded fibers from the fiber sample comprises placing the fiber sample in a solvent to produce a solution comprising a dissolved portion of the fiber sample and the branded fibers and removing the branded fibers from the solution.

In one aspect the standard fibers comprise cellulose acetate and the fiber sample comprises a portion of an article comprising the fibers. In some aspects the article can be selected from the group consisting of a filter rod and a cigarette filter. In other aspects, the fiber sample comprises a portion of an article comprising the fibers, wherein the article is selected from the group consisting of fabrics and other textile products, non-wovens, and absorbent products.

In one aspect, the imaging technology comprises the use of electromagnetic radiation at visible wavelengths. In another aspect, the image technology comprises the use of electromagnetic radiation at invisible wavelengths. The equipment useful for imaging technology is not particularly limited. Non-limiting examples include human visual inspection, microscopy, electron microscopy, confocal microscopy, and optical scanning.

The imaging technology can be applied to the fiber sample parallel to the length of the fibers. This direction allows, for example, a view of a pattern of surface markings on the fibers.

The imaging technology may also be applied to the article comprising the fibers, fiber band, or yarn.

In one aspect, the method for characterizing the fiber sample further comprises (a) correlating the taggant surface markings and/or the repeated pattern of the taggant surface markings to a database comprising manufacturer-specific taggants; and (b) determining at least one supply chain component of the fiber sample. The supply chain component comprises a manufacturer of the standard fibers, a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a yarn or fiber band comprising the fibers, a manufacturing site of the yarn or fiber band, a manufacturing line of the yarn or fiber band, a production run of the yarn or fiber band, a production date of the yarn or fiber band, a package of the yarn or fiber band, a warehouse of the yarn or fiber band, a customer of the yarn or fiber band, a ship-to location of the yarn or fiber band, a manufacturer of an article comprising the fibers, a manufacture site of the article, a manufacturing line of the article, a production run of the article, a production date of the article, a package of the article, a warehouse of the article, a customer of the article, or a ship-to location of the article. In one aspect the correlating is among the distinct features and/or the combinations of distinct features. In another aspect, the correlating is among the distinct features, the combinations of distinct features, and/or the total number of each of the distinguishable identification fibers. In another aspect, the correlating is among the distinct features, the combinations of distinct features, the total number of each of the distinguishable identification fibers, and/or the taggant total identification fiber number. In one aspect, at least one supply chain component comprises a manufacturer of a yarn comprising the fibers, a manufacturing site of the yarn, a manufacturing line of the yarn, a production run of the yarn, a production date of the yarn, a package of the yarn, a warehouse of the yarn, a customer of the yarn, a ship-to location of the yarn.

In one aspect, the supply chain information comprises the manufacturer of the yarn or fiber band. In one aspect, the supply chain information comprises the manufacture site of the yarn or fiber band. In one aspect the supply chain information comprises the manufacturing line of the yarn or fiber band. The manufacturing line of the yarn or fiber band is the manufacturing line on which the yarn or fiber band was produced. In one aspect, the supply chain information comprises the production run of the yarn or fiber band. The production run of the yarn or fiber band is the production run within which the yarn or fiber band was produced. In one aspect, the supply chain information comprises the production date of the yarn or fiber band. The production date of the yarn or fiber band is the production date on which the yarn or fiber band was produced. In one aspect, the supply chain information comprises the bale of the yarn or fiber band. In one aspect, the supply chain information comprises the customer of the yarn or fiber band. The customer of the yarn or fiber band is the customer to whom the manufacturer plans to send or has sent the yarn or fiber band. In one aspect, the supply chain information comprises the ship-to location of the yarn or fiber band. The ship-to location of the yarn or fiber band is the specific geographic location to which the manufacturer plans to send or has sent the yarn or fiber band.

In one aspect the fiber sample comprises a portion of a filter, comprising an acetate tow band, wherein the method further comprises correlating the repeated pattern of taggant surface markings to a database comprising manufacturing specific taggants, and wherein the at least one supply chain component comprises a bale of the acetate tow band.

The disclosed embodiments also include making an article with fibers, a fiber band, and/or yarn having any of the disclosed features. The disclosed embodiments also include characterizing an article comprising a fibers, fiber band, or yarn having any of the disclosed features.

Figure 5A:
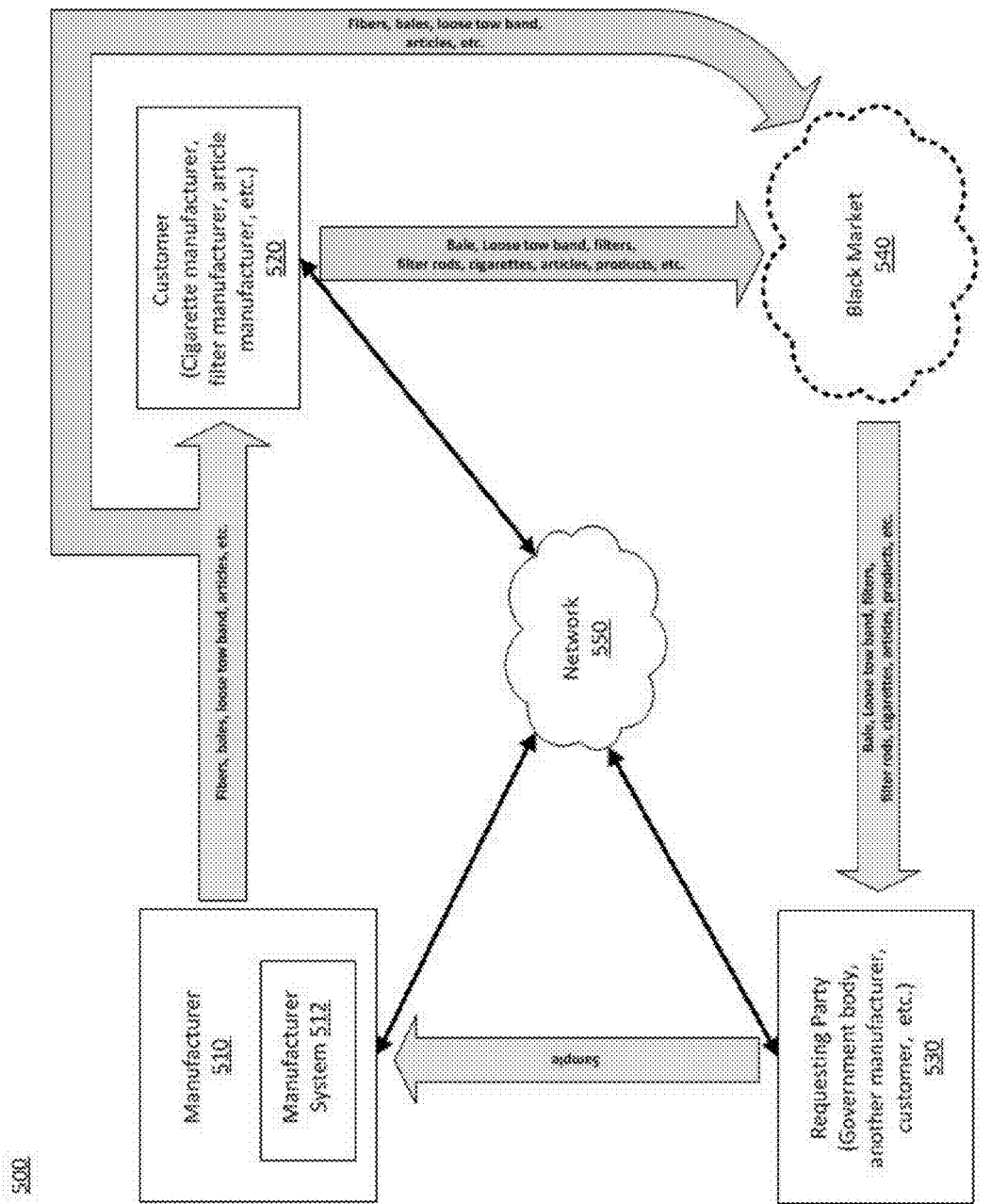
FIGS. 5A and 5B illustrate non-limiting examples of communication and shipping channels among one or more entities consistent with disclosed embodiments
Figure 5B:
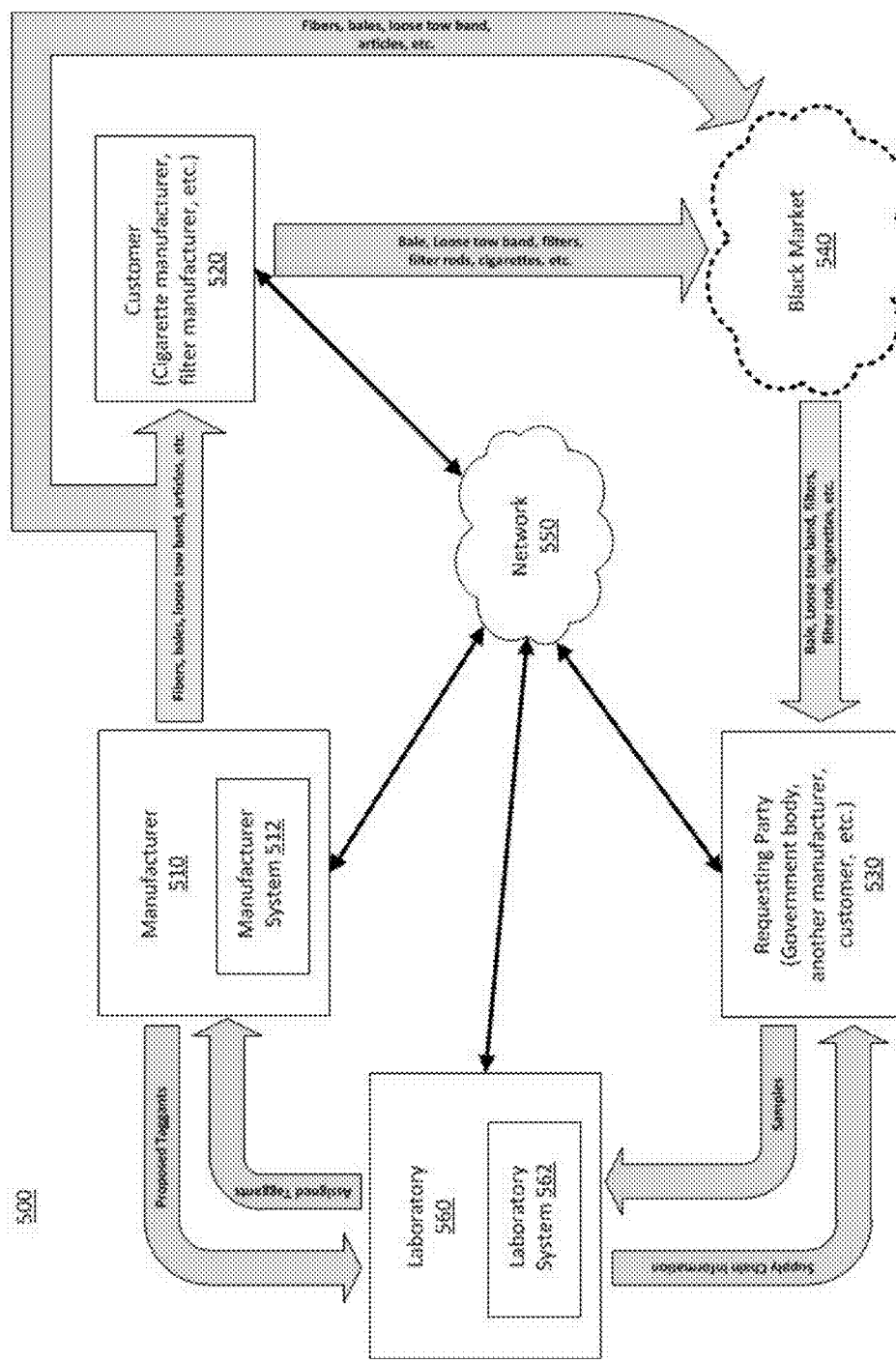

FIGS. 5A and 5B illustrate non-limiting examples of an environment 500 depicting communication and shipping channels among entities consistent with disclosed embodiments. In one embodiment, environment 500 of FIGS. 5A and 5B may include one or more manufacturers 510, one or more customers 520, a black market 540 or other illicit trade network, one or more requesting parties 530, one or more laboratories 560, and communication network 550. The components and arrangement of the components included in environment 500 (e.g., as illustrated in FIGS. 5A and 5B) may vary. Thus, environment 500 may include other components that perform or assist in the performance of one or more processes consistent with the disclosed embodiments.

In some aspects, network 550 may be any type of network configured to provide communication means between systems of components of environment 500 (e.g., manufacturing system 512 and/or laboratory system 562). For example, network 550 may be any type of network (including infrastructure) that facilitates communications, exchanges information, etc., such as the Internet, a Local Area Network, near field communication, and/or other suitable connection(s) that enables the sending and receiving of information between the components systems associated with environment 500. In other embodiments, one or more component systems of environment 500 may communicate directly through a dedicated communication link(s), such as links between manufacturer 510, customer 520, requesting party 530, and/or laboratory 560.

Further, and as stated above, manufacturers (e.g., manufacturer 510) may produce cellulose acetate fibers and fiber products that incorporate the cellulose acetate fibers on an industrial scale. In some embodiments, the produced cellulose acetate fibers and fiber products may include standard fibers and identification fibers. Each of the identification fibers exhibits one or more distinct features (e.g., distinct cross-section sizes, distinct cross-section shapes, distinct optical properties, and additionally or alternatively, distinct surface markings.) that visually distinguish the identification fibers from the standard fibers. In some aspect, one or more of the distinct surface markings may represent a taggant surface markings, and the identification fibers may include one or more branded fibers that exhibit one or more of the taggant surface markings. The taggant surface markings exhibited by the branded fibers may, in certain aspects, form a repeated pattern disposed along the length of the branded fibers. The repeated pattern may, for example, be representative of at least one supply chain component associated with the standard fibers, the identification fibers, and/or fibers and fiber products that include the standard and/or identification fibers.

In other aspects, the repeated pattern may be representative of a code associated with the identification fibers and/or the standard fibers (e.g., an alphanumeric code, a digital code, an analog code, and/or an ideographic code, as described above). In some embodiments, portion of the code may be representative of at least one supply chain component associated with the standard fibers, the identification fibers, and/or fibers and fiber products that include the standard and/or identification fibers.

In some embodiments, the inclusion of identification fibers in the cellulose acetate fibers may enable manufacturer 510 to tag the cellulose acetate fibers, and thus, the fiber products that include the cellulose acetate fibers, with supply chain information prior to shipment to customers 520. By way of example, fiber products consistent with the disclosed embodiments may include, but are not limited to, cellulose acetate tow, loose bands of cellulose acetate tow, bales of cellulose acetate tow, and fabrics and other articles that include the cellulose acetate fibers and/or tow.

For example, and in the context of cigarette manufacturing, customer 520 may use a bale of acetate tow to produce various intermediate and/or final stage products (e.g., loose tow band, filter rods, filters, and/or cigarettes) and a fraction of these products can ultimately find their way onto the black market (e.g., black market 440). Thus, because supply chain information can be determined from a sample of any black market product having tagged identification fibers, a party interested in combating illicit trade (e.g., requesting party 530) may obtain a black market product and submit a sample for analysis in order to identify supply chain information associated with the black market product.

Thus, in one embodiment, requesting party 530 may provide the sample to manufacturer 510, as depicted in FIG. 5A. Manufacturer 510 may, in certain aspects, analyze the sample using any of the exemplary techniques outlined above to identify at least one component of a supply chain associated with the sample. For example, the sample may include standard and identification fibers, which may include branded fibers exhibiting one or more taggant surface markings that form a repeated pattern along a length of the branded fibers. Based on the analysis, manufacturer 510 may identify, within the identification fibers, the one or more branded fibers that exhibit the one or more taggant surface markings. Manufacturer 510 may also identify the repeated pattern formed by the taggant surface markings along the length of the branded fibers (e.g., through an application of an imaging technology to the branded fibers, as described above).

In certain aspects, manufacturer 510 may access correlation data mapping components of the supply chain to the exhibited taggant surface markings and additionally or alternatively, to the identified repeated pattern formed by the taggant surface markings along the length of the branded fibers. Manufacturer 510 may identify the at least one component of the supply chain based on, for example, a comparison of the exhibited taggant surface markings and/or the identified repeated pattern to the accessed correlation data. In some instances, manufacturer 510 may transmit information identifying the at least one supply chain component to requesting party 530 (e.g., across network 550).

In the exemplary embodiments described above, manufacturer 510 may analyze the sample to identify at least one component of a supply chain associated with the sample. The disclosed embodiments are, however, not limited to exemplary analyses conducted by manufacturer 510, and in further embodiments, customer 520, requesting party 530, or a third-party (not shown) may conduct the analysis for identifying supply chain information from tagged fibers.

For example, as illustrated in FIG. 5B, a laboratory 560 may act on behalf of requesting party 530 and perform the analysis on the sample to identify the at least one supply chain component associated with the sample. In some instances, laboratory 560 may represent a governmental entity, a quasi-governmental entity, or a private entity capable of performing the analysis, and requesting party 530 may contract with or retain laboratory 560 to perform the analysis on a one-time or recurring basis.

In other instances, however, laboratory 560 may be established by one of more of manufacturer 510, customers 520, and/or requesting party 530 in order to regularly and reliably identify supply chain components associated with samples taken from illicitly traded cellulose acetate fibers or fiber products that incorporate the cellulose acetate fibers (e.g., as obtained by requesting party 530 from black market 540). Laboratory 560 may, in certain aspects, perform the analysis of the sample in accordance with one or more procedures established by a manufacturer 510, customers 520, and/or requesting party 530. For example, one or more of manufacturer 510, customers 520, and/or requesting party 530 may collectively establish standardized procedures and protocols for receiving and handling samples, analyzing the samples to identify the supply chain components in an accurate and repeatable manner, and reporting portions of the identified supply chain components to manufacturer 510, customers 520, and/or requesting party 530. Further, in additional embodiments, laboratory 560 may also assign the taggant surface markings, repeated patterns formed by taggant surface markings, and/or portions of the codes represented by the repeated patterns to various components of the supply chain (e.g., manufacturers) to uniquely identify these supply chain components. In further embodiments, customer 520, requesting party 530, or a third-party (not shown) may assign the taggant surface markings, repeated patterns formed by taggant surface markings, and/or portions of the codes represented by the repeated patterns to various components of the supply chain (e.g., manufacturers) to uniquely identify these supply chain components.

In one embodiment, as illustrated in FIG. 5B, requesting party 530 may provide the sample to laboratory 560. Laboratory 560 may, in certain aspects, analyze the sample to identify at least one component of a supply chain associated with the sample (e.g., a manufacturer). For example, using any of exemplary techniques described above, laboratory 560 may analyze the sample to identify the identification fibers that exhibit one of more distinct features, including, for example, one or more branding fibers that exhibit one or more taggant surface markings. Laboratory 560 may further identify one or more repeated patterns formed by the taggant surface markings along the length of the branded fibers. Further, laboratory 560 may access correlation data, and using any of the exemplary techniques described above, identify the at least one supply chain component based on a comparison of the exhibited taggant surface markings and the identified repeated patterns to the accessed correlation data.

In additional embodiments, laboratory 560 may function as a centralized facility that assigns unique taggant surface markings, unique repeated patterns, and unique codes (or portions of codes) represented by the repeated patterns to various components of the supply chain (e.g., to manufacturer 510). For example, laboratory 560 may assign, to manufacturer 510, a taggant surface marking, a repeated pattern formed by the assigned taggant surface marking, and/or a portion of a code represented by the assigned repeated pattern.

When exhibited by branded fibers included within cellulose acetate fibers and corresponding fiber products produced by manufacturer 510, the assigned taggant surface marking, assigned repeated pattern, and/or assigned code portion may uniquely represent manufacturer 510 and may enable laboratory 560 (and additionally or alternatively, any other entity within environment 500) to identify manufacturer 510 as a source of the fibers or fiber products using any of the analytical techniques described above. Further, laboratory 560 (and additionally or alternatively, any other entity within environment 500) may also establish and maintain data records (e.g., within a centralized database implemented using the exemplary computing systems outlined below) that identify a correlation between the various supply chain components (e.g., manufacturer 510) and corresponding ones of the assigned taggant surface markings, repeated patterns, and/or code and code portions.

The disclosed embodiments are, however, not limited to the assignment of exemplary taggant surface markings, exemplary repeated patterns, and/or exemplary code and code portions to manufacturer 510. In further embodiments, laboratory 560 may assign any additional or alternate taggant information, and further, any additional or alternate set or combinations of sets of taggant surface markings, repeated patterns, and/or code and code portions to uniquely identify manufacturer 510.

In certain aspects, laboratory 560 may establish a centralized repository for data and data records (e.g., using any of the exemplary computing systems outlined below) that correlate the various supply chain components (e.g., manufacturer 510) to corresponding ones of taggant surface markings, repeated patterns formed by taggant surface markings, and/or codes and code portions represented by the repeated patterns. Further, in other aspects, laboratory 560 may access the centralized repository and generate one or more reports specifying the taggant surface markings, repeated patterns formed by the taggant surface markings, and/or codes represented by the repeated patterns that uniquely identify at least one of the supply chain components (e.g., manufacturers). Laboratory 560 may, in some instances, generate the reports at predetermined intervals or in response to received requests (e.g., from requesting party 530, manufacturer 510, etc.), and may provide the generated reports to various parties and entities within environment 500 (e.g., across network 550).

In some embodiments, laboratory 560 may access the centralized repository to identify at least one supply chain component (e.g., manufacturer 510) associated with taggant surface markings and/or a repeated patterns formed by the taggant surface markings determined by laboratory 560 (e.g., using any of the analytical techniques outlined above) and additionally or alternatively, obtained from any third party or other entity within environment 500. Further, and as described below, the centralized repository may enable laboratory 560 to determine whether proposed taggant surface markings, proposed repeated patterns capable of being formed by the taggant surface markings, and/or proposed codes representable by the repeated patterns (e.g., as selected by manufacturer 510) are capable of uniquely representing fibers and fiber products of manufacturer 510 that are introduced into the supply chain.

In certain embodiments, laboratory 560 may receive one or more proposed taggant surface markings, a proposed repeated pattern, and/or a proposed code (or code portion) representable by the proposed repeated pattern from manufacturer 510. Laboratory 560 may, for example, compare the proposed taggant surface markings, proposed repeated pattern, and/or proposed code (or code portion) against the established data records (e.g., within the centralized repository) to determine whether these the proposed taggant surface markings, proposed repeated pattern, and/or proposed code (or code portion) are capable of uniquely identifying manufacturer 510 (e.g., the proposed taggant surface markings, proposed repeated pattern, and/or proposed code (or code portion) are assigned to no other supply chain components, such as another manufacturer). If the proposed taggant surface markings, proposed repeated pattern, and/or proposed code (or code portion) could uniquely represent manufacturer 510, laboratory 560 may assign the proposed taggant surface markings, proposed repeated pattern, and/or proposed code (or code portion) to manufacturer 510, update the data records to reflect the assignment, and provide confirmation of the assignment to manufacturer 510 (e.g., between computing systems of laboratory 560 and manufacturer 510 across network 550).

Alternatively, if laboratory 560 previously assigned the proposed taggant surface markings, proposed repeated pattern, and/or proposed code (or code portion) to another manufacturer (or the proposed taggant surface markings, proposed repeated pattern, and/or proposed code (or code portion) are inappropriate to represent manufacturer 510), laboratory 560 may assign one or more alternate taggant surface markings, an alternate repeated pattern, and/or an alternate code (or code portion) representable by the alternate repeated pattern to manufacturer 510, update the data records to reflect the alternate assignment, and provide confirmation of the alternate assignment to manufacturer 510. In other aspects, laboratory 560 could provide, to manufacturer 510, an indication of the assignment of the proposed taggant surface markings, proposed repeated pattern, and/or proposed code (or code portion) to another manufacturer, and request that manufacturer 510 propose one or more additional taggant surface markings, an additional repeated pattern, and/or an additional code (or code portion) representable by the additional repeated pattern for assignment by laboratory 560, as described above.

In certain aspects, upon confirmation of the assignment, manufacturer 510 may obtain and/or produce branded fibers exhibiting the assigned taggant surface markings, which form the assigned repeated pattern, and which represent the assigned code and/or code portion. In other aspects, however, manufacturer 510 may further correlate the assigned taggant surface markings, the assigned repeated patterns, and/or the assigned code (or code portion) represented by the assigned repeated patterns to one or more upstream components of the supply chain (e.g., a manufacture site, a manufacturing line, a production run, a production date, a bale) and/or various downstream components of the supply chain (e.g., a warehouse, a customer, a ship-to location, etc.).

For example, manufacturer 510 may further specify that additional code or code portions associated with the assigned repeated pattern (i.e., code portions distinct from those representing manufacturer 510) uniquely represent a particular customer within the supply chain (e.g., customer 520) or a particular bale produced and shipped by manufacturer 510.

The disclosed embodiments are, however, not limited to techniques that enable manufacturer 510 to correlate customer 520 and/or a particular bale to the assigned taggant surface markings, the assigned repeated patterns, and/or the assigned code (or code portion) represented by the assigned repeated patterns. In further embodiments, manufacturer 510 may specify any additional or alternate taggant information (e.g., distinct features, combinations of distinct features, etc.) to represent other upstream or downstream supply components (or combinations thereof) in conjunction with the assigned taggant surface markings, the assigned repeated patterns, and/or the assigned code (or code portion) represented by the assigned repeated patterns.

In some aspects, while laboratory 560, or another entity, may maintain information linking manufacturer 510 to assigned taggant surface markings, the assigned repeated patterns, and/or the assigned code (or code portion) represented by the assigned repeated patterns, manufacturer 510 may hold confidential additional taggant information (e.g., distinct features, combinations of distinct features, non-assigned code portions, etc.) that links identification fibers, and thus fiber products produced by manufacturer 510, to other upstream and downstream components of the supply chain. The confidentiality of the additional taggant information may, in certain instances, enable manufacturer 510 to prevent laboratory 560 from identifying customers (e.g., customer 520), ship-to locations, warehouses, and other internal supply chain components (e.g., manufacture site or line, and production run or date) associated with manufacturer 510.

The embodiments described above identify particular combinations of taggant information that correlate to a specific component of a supply chain and, when exhibited in identification fibers of a sample, enable a laboratory, a manufacturer, or other entities to identify the specific supply chain component associated with the sample. One of ordinary skill in the art would, however, understand that the disclosed embodiments are not limited to the particular combinations or taggant information outlined above, and in further embodiments, specific supply chain components may be correlated with any additional or alternate physical, chemical, and/or optical characteristic exhibited by the identification fibers, which include, but are not limited to, distinct features, and/or combinations of distinct features. Moreover, while not depicted in FIGS. 5A and 5B, one of skill in the art would understand that entities associated with environment 500 (shown and not shown) may employ one or more warehouses to store raw materials, intermediate products, final stage products, etc. in conducting operations consistent with disclosed embodiments.

Further, the disclosed embodiments are, however, not limited to the assignment of taggant surface markings, repeated patterns, and/or codes and code portions to various components of the supply chain (e.g., manufacturers). In further embodiments, manufacturer 510, laboratory 560, customers 520, requesting party 530, or a third-party (not shown) may assign other taggant information to the various components of the supply chain, which include, but are not limited to, distinct features, and/or combinations of distinct features.

Figure 6:
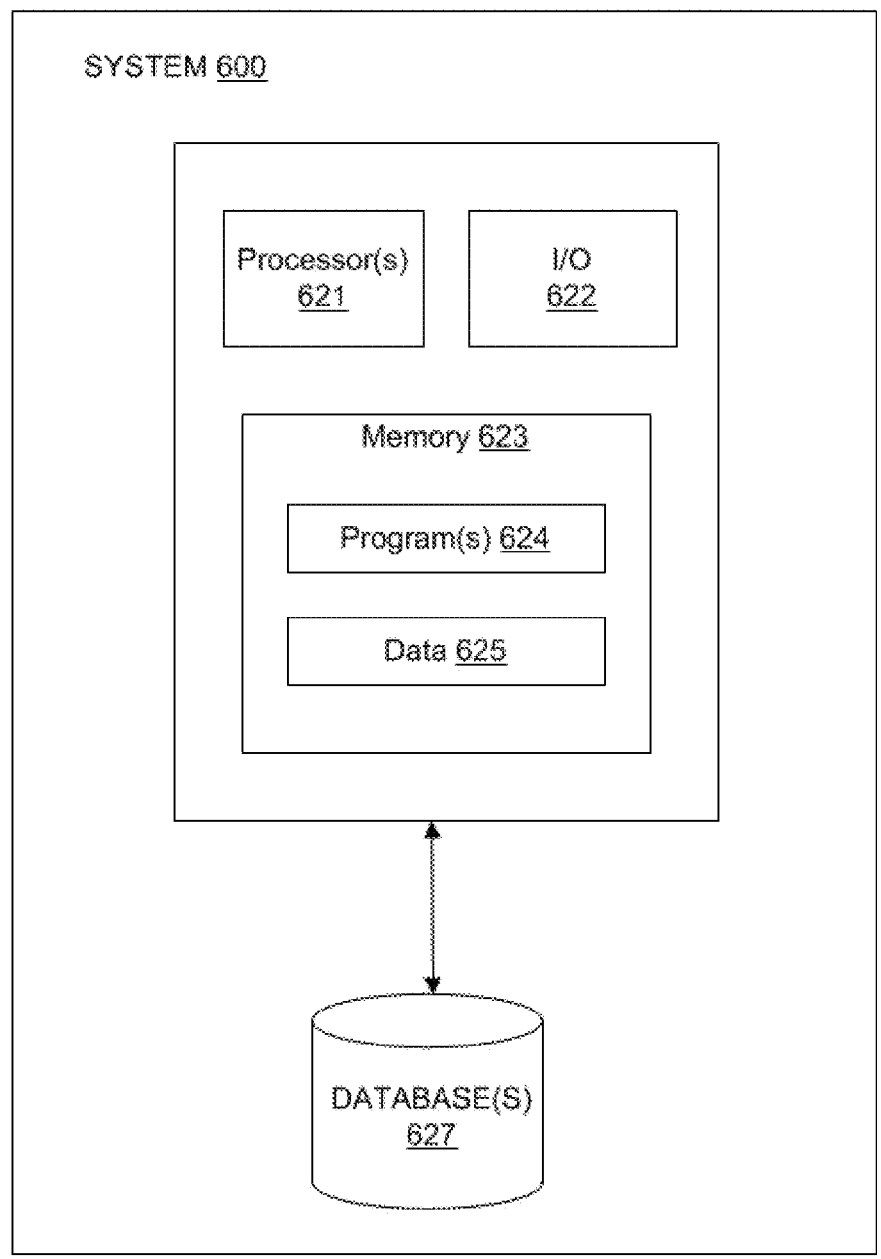
FIG. 6 illustrates a non-limiting example of a computing system used by one or more entities consistent with disclosed embodiments.

FIG. 6 illustrates a non-limiting example of a computing system 600 used by one or more entities consistent with disclosed embodiments. Variations of exemplary system 600 may be used by manufacturer 510 (e.g., as manufacturer system 512), customer 520, requesting party 530, and/or laboratory 560 (e.g., as laboratory system 562). In one embodiment, system 600 may comprise one or more processors 621, one or more input/output (I/O) devices 622, and one or more memories 623. In some embodiments, system 600 may take the form of a server, mainframe computer, or any combination of these components. In some embodiments, system 600 may take the form of a mobile computing device such as a smartphone, tablet, laptop computer, or any combination of these components. Alternatively, system 600 may be configured as a particular apparatus, embedded system, dedicated circuit, and the like based on the storage, execution, and/or implementation of the software instructions that perform one or more operations consistent with the disclosed embodiments.

Processor 621 may include one or more known processing devices, such as mobile device microprocessors or any various other processors. The disclosed embodiments are not limited to any type of processor(s) configured in system 600.

Memory 623 may include one or more storage devices configured to store instructions used by processor 624 to perform functions related to the disclosed embodiments. For example, memory 623 may be configured with one or more software instructions, such as program(s) 624 that may perform one or more operations consistent with disclosed embodiments when executed by processor 621. The disclosed embodiments are not limited to separate programs or computers configured to perform dedicated tasks. For example, memory 623 may include a single program 624 that performs the functions of system 600, or program 624 may comprise multiple programs. Memory 623 may also store data 625 that is used by one or more programs 612, such as correlation data mapping distinct features to one or more components of the supply chain information.

I/O devices 622 may be one or more devices configured to allow data to be received and/or transmitted by system 600. I/O devices 622 may include one or more digital and/or analog devices that allow components of environment 500 to communicate with other machines and devices, such as other components of environment 500. For example, I/O devices 622 may include a screen for displaying messages, distinct feature information, supply chain information, or providing other information to the user, such as an employee of manufacturer 510, customer 520, requesting party 530, and/or laboratory 560. I/O devices 622 may also include one or more digital and/or analog devices that allow a user to interact with system 600 such as a touch-sensitive area, keyboard, buttons, or microphones. I/O devices 622 may also include other components known in the art for interacting with a user.

The components of system 600 may be implemented in hardware, software, or a combination of both hardware and software, as will be apparent to those skilled in the art. For example, although one or more components of system 600 may be implemented as computer processing instructions, all or a portion of the functionality of system 600 may be implemented instead in dedicated electronics hardware.

System 600 may also be communicatively connected to one or more database(s) 627. System 600 may be communicatively connected to database(s) 627 through network 550. Database 627 may include one or more memory devices that store information and are accessed and/or managed through system 600. By way of example, database(s) 627 may include Oracle™ databases, Sybase™ databases, or other relational databases or non-relational databases, such as Hadoop sequence files, HBase, or Cassandra.

The databases or other files may include, for example, data and information related to distinct features, supply chain information, correlation data mapping the distinct features (e.g., taggant surface marking(s)), repeated pattern(s) formed by taggant surface markings, and/or code(s) associated with the repeated pattern(s) to the supply chain information, data indicative of distinct features (e.g., taggant surface marking(s)), repeated pattern(s) formed by taggant surface markings, and/or code(s) associated with the repeated pattern(s) assigned to the supply chain information, etc. For example, the databases and other files may include correlation data mapping the supply chain components to distinct features (e.g., taggant surface marking(s)), repeated pattern(s) formed by taggant surface markings, and/or code(s) associated with the repeated pattern(s) included in fiber samples, as described above. Further, by way of example, the databases and other files may also include distinct features (e.g., taggant surface marking(s)), repeated pattern(s) formed by taggant surface markings, and/or code(s) associated with the repeated pattern(s) included in fiber samples assigned to supply chain components by laboratory 560, as outlined above.

Systems and methods of disclosed embodiments, however, are not limited to separate databases. In one aspect, system 600 may include database 627. Alternatively, database 627 may be located remotely from the system 600. Database 627 may include computing components (e.g., database management system, database server, etc.) configured to receive and process requests for data stored in memory devices of database(s) 627 and to provide data from database 627.

Although the above description has designated laboratory 560 as the entity assigning various taggants, in other aspects, manufacturer 510, customer 520, requesting party 530 or a third-party entity not shown may be the one assigning taggants for identification fibers. Furthermore, as seen from FIGS. 5A and 5B, although the description has focused on cellulose acetate tow and the black market associated with cigarette filters, the embodiments clearly apply to fibers of any material and any article subject to illicit trade.

Figure 7:
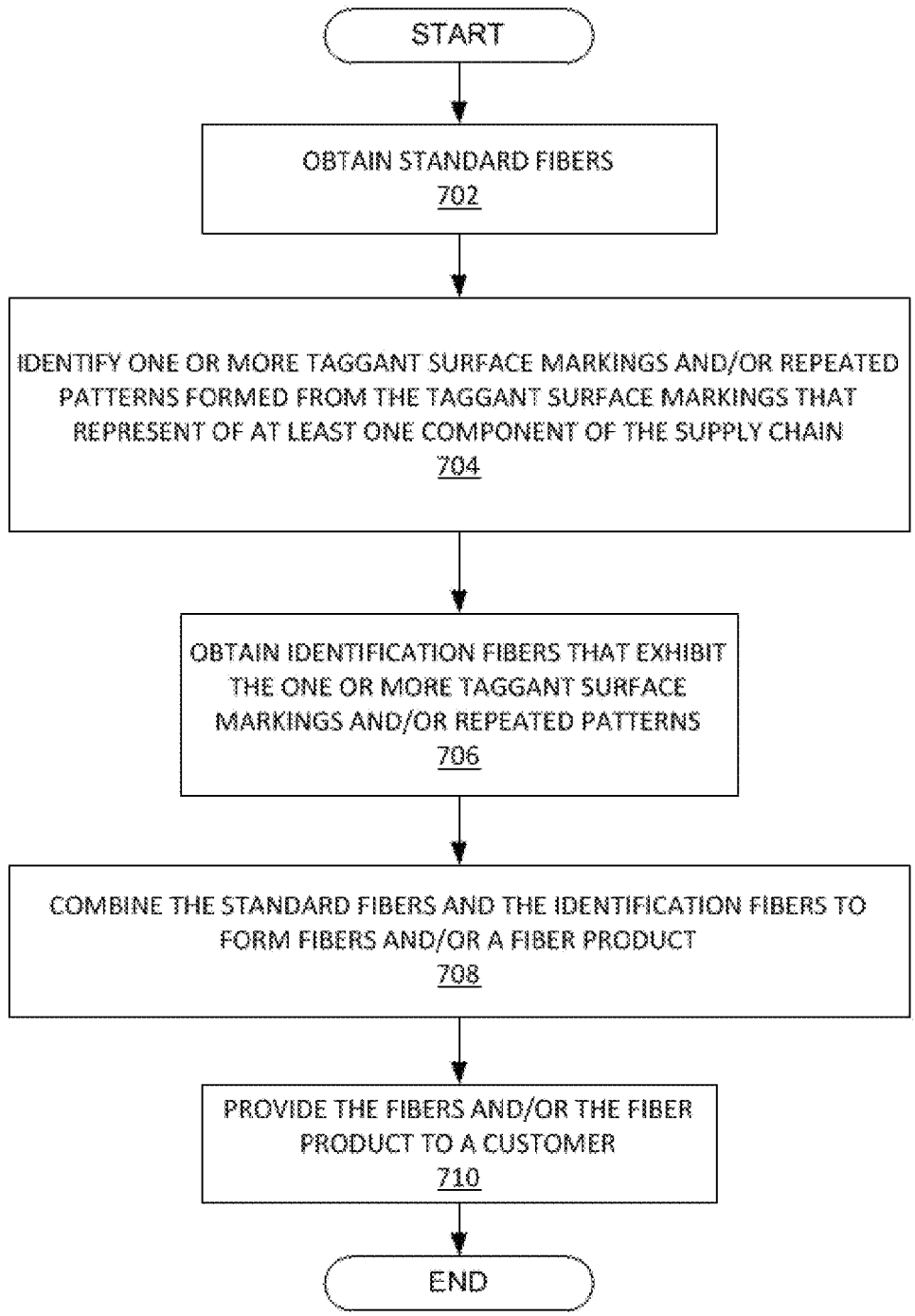
FIG. 7 illustrates a non-limiting example of a process for embedding supply chain information into fibers, consistent with disclosed embodiments.

FIG. 7 illustrates a non-limiting example of a process for embedding supply chain information into fibers, as seen and described above with respect to disclosed embodiments.

Figure 8:
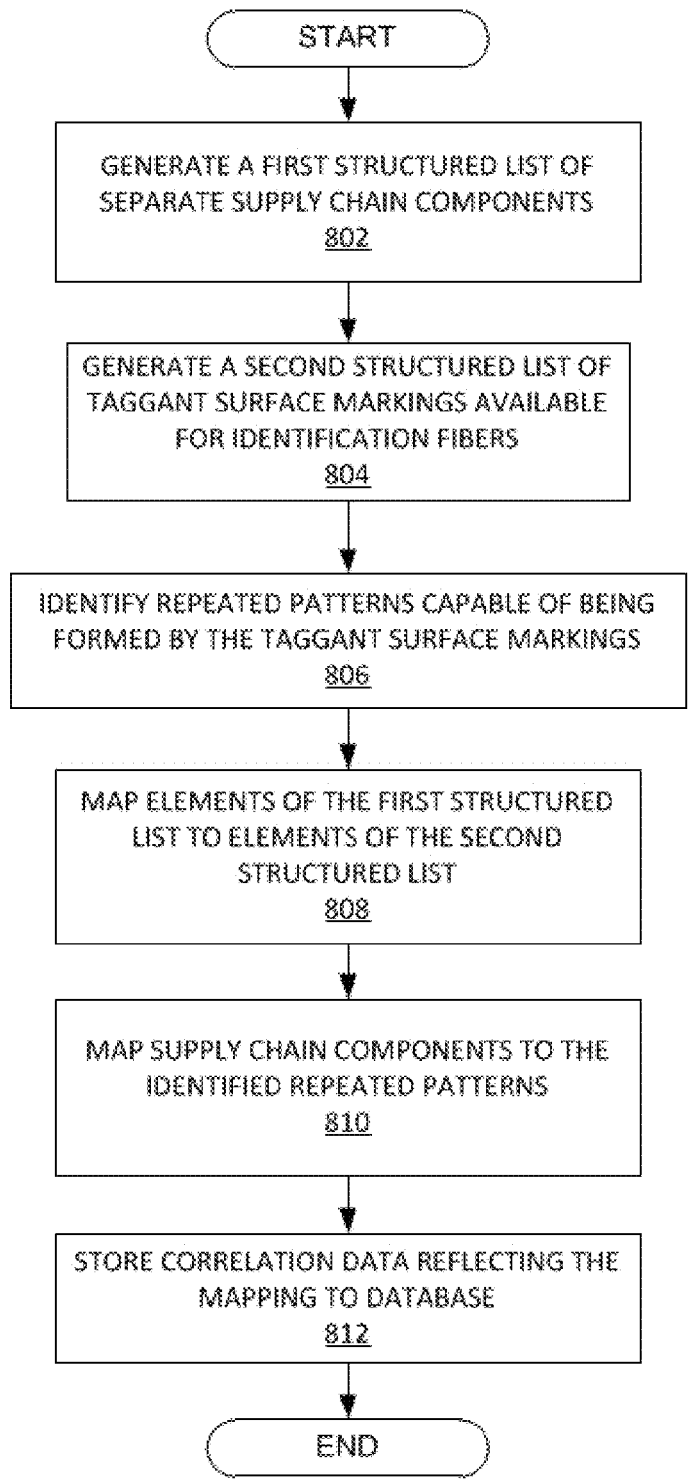
FIGS. 8 and 9 illustrate non-limiting examples of processes for generating correlation data, consistent with disclosed embodiments.

FIG. 8 illustrates a non-limiting example of a process for generating correlation data, as seen and described above with respect to disclosed embodiments. For example, as described in FIG. 8, manufacturer 510 (and additionally or alternatively, laboratory 560) may generate a first structured list of the supply chain components having one or more corresponding attributes, and may generate a second structured list of taggant surface markings available for application to or inclusion within identification fibers. In one instance, the supply chain components may represent one or more corresponding attributes. Manufacturer 510 may identify repeated patterns capable of being formed by the taggant surface markings along lengths of identification fibers (i.e., branded fibers). In some aspects, manufacturer 510 may map elements of the first structured list to elements of the second structured list, and may map the supply chain components of the first structured list to the identified repeated patterns. Manufacturer 510 may, in additional aspects, store correlation data (e.g., in database 627) reflecting the mapping of the elements of the first and second structured lists.

Figure 9:
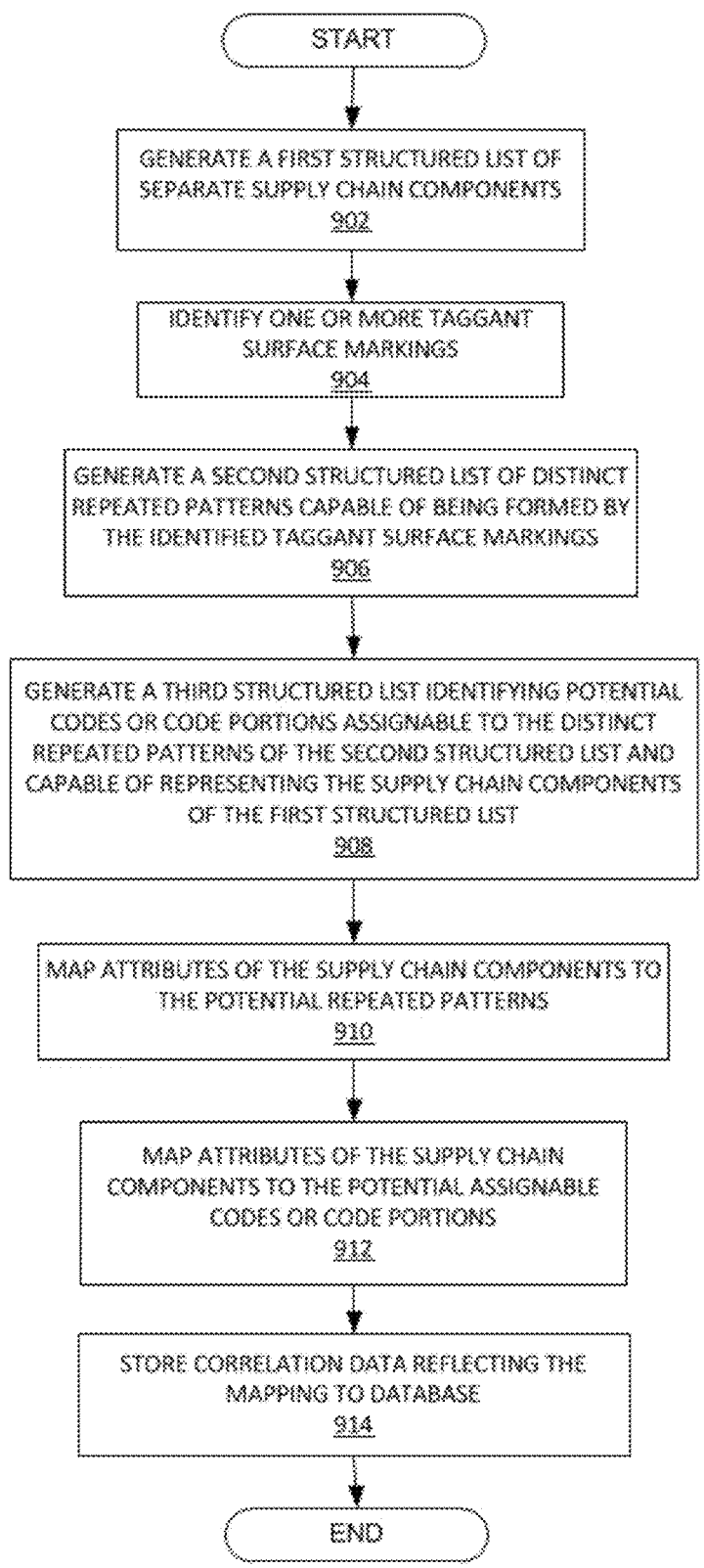

FIG. 9 illustrates an additional non-limiting example of a process for generating correlation data, as seen and described above with respect to disclosed embodiments. For example, as described in FIG. 9, laboratory 560 (and additionally or alternatively, manufacturer 510) may generate a first structured list of components of the supply chain. In one instance, the supply chain components may represent one or more corresponding attributes. Laboratory 560 may also identify one or more taggant surface markings appropriate for application to or inclusion within identification fibers (i.e., branded fibers), and may generate a second structured list that includes potential repeated patterns capable of being formed by the identified taggant surface markings. In some aspects, laboratory 560 may generate a third structured list identifying potential codes or code portions that are assignable to the potential repeated patterns of the second structured list and capable of representing the supply chain components of the first structured list Laboratory 560 may further map elements of the first structured list to elements of the second structured list, and further map elements of the first structured list to elements of the third structured list. In some aspects, laboratory 560 may store correlation data (e.g., in database 627) reflecting the mappings of the attributes of the supply chain components to the potential repeated patterns and potential code and code portions.

Figure 10:
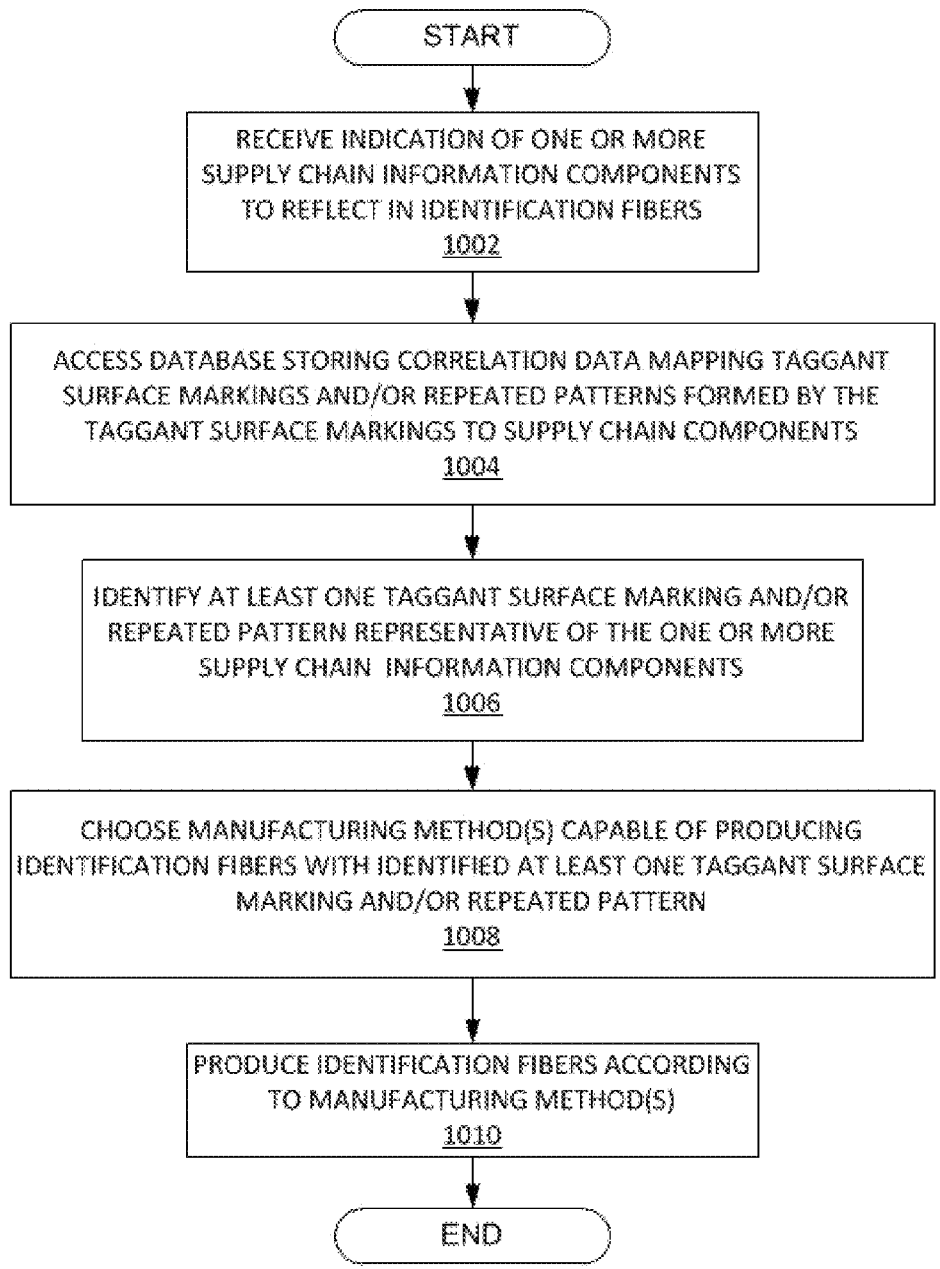
FIG. 10 illustrates a non-limiting example of a process for producing identification fibers, consistent with disclosed embodiments.

FIG. 10 illustrates a non-limiting example of a process for producing identification fibers, as seen and described above with respect to disclosed embodiments.

Figure 11:
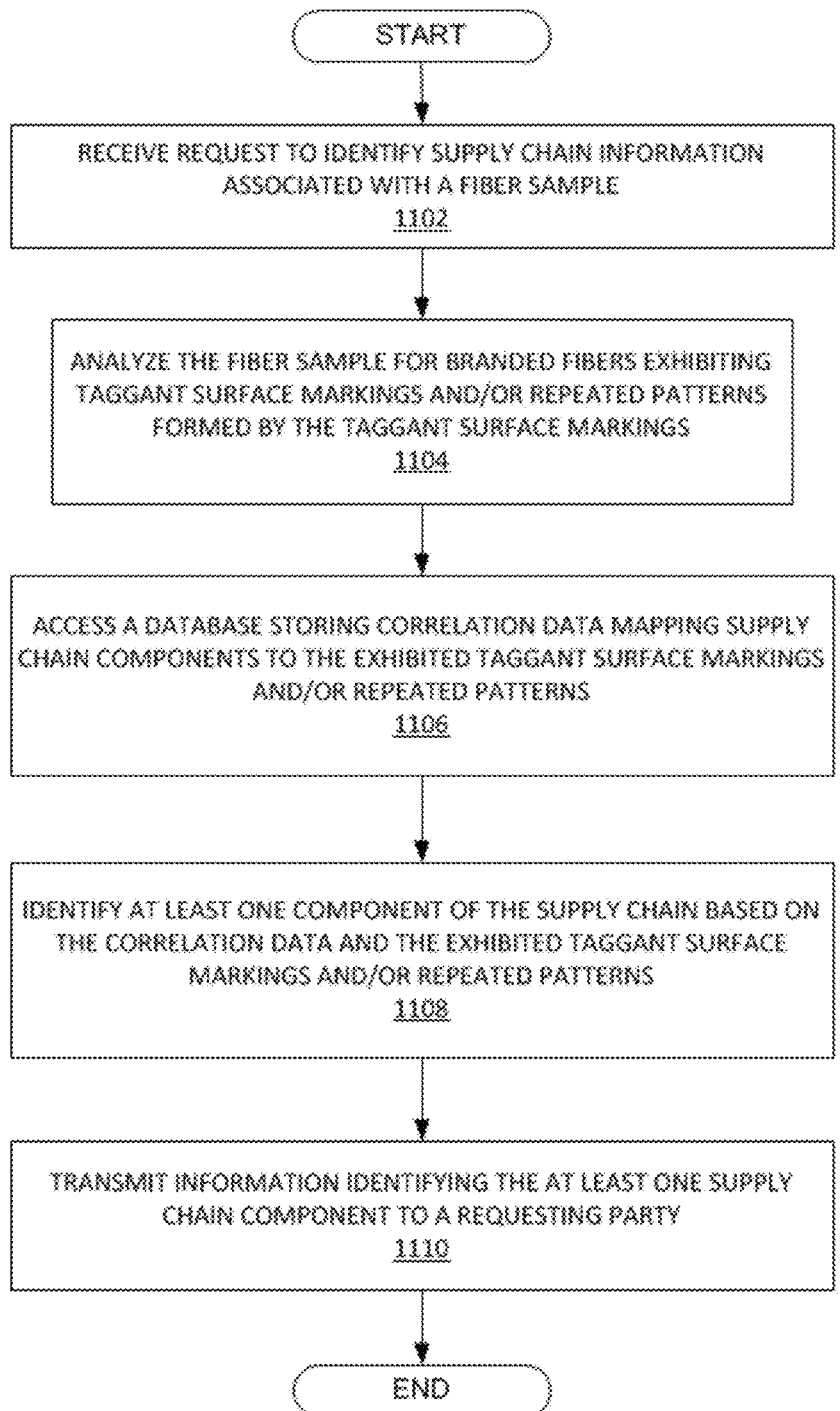
FIG. 11 illustrates a non-limiting example of a process for identifying supply chain information from a sample, consistent with disclosed embodiments.

FIG. 11 illustrates a non-limiting example of a process for identifying at least one supply chain component associated with a fiber sample, as seen and described above with respect to disclosed embodiments.

Figure 12:
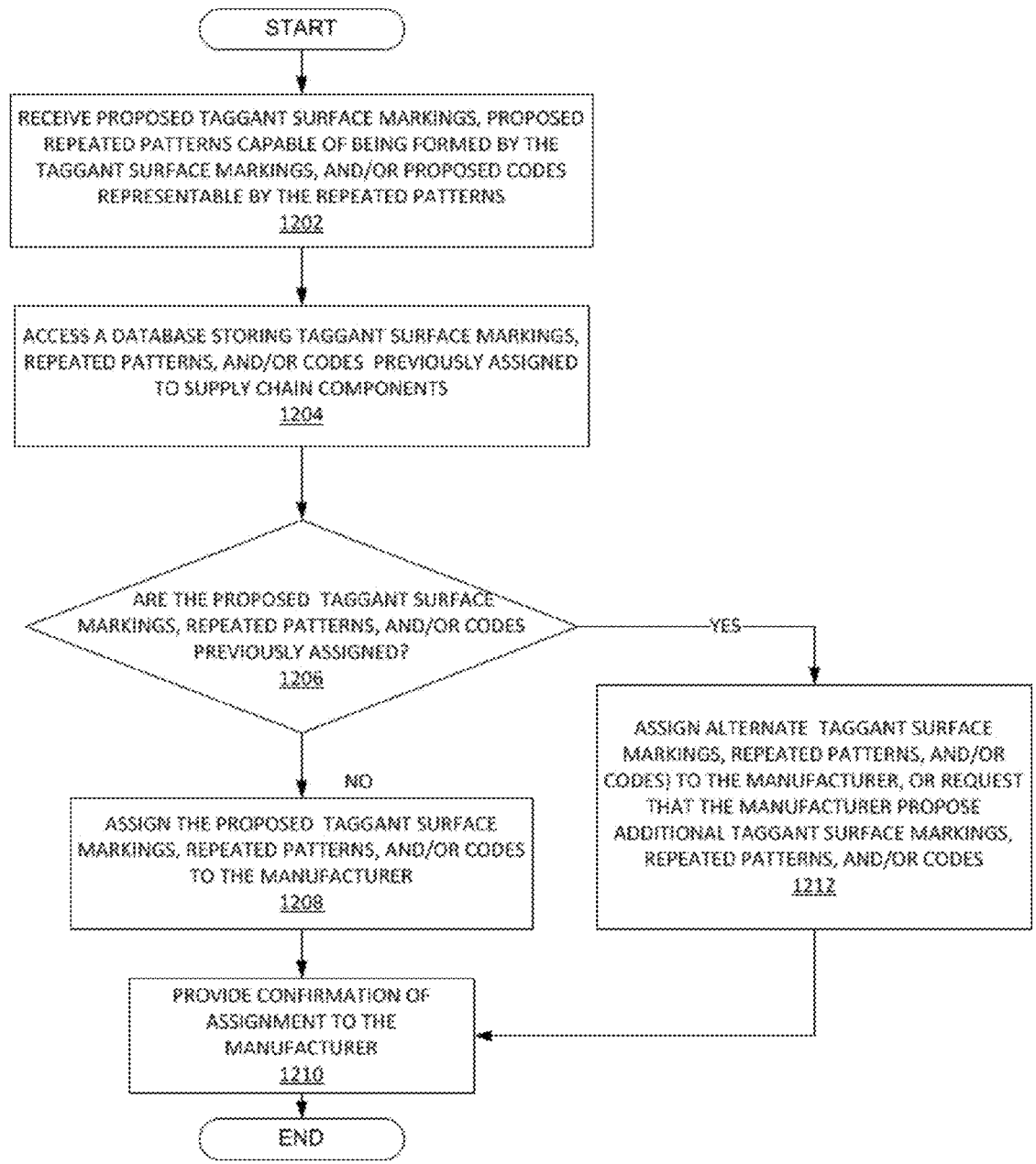
FIG. 12 illustrates a non-limiting example of a process for assigning taggant information to supply chain components, consistent with disclosed embodiments.

FIG. 12 illustrates a non-limiting example of a process for assigning, to supply chain components, taggant surface markings, repeated patterns, and code and code portions that uniquely represent the supply chain components, as seen and described above with respect to disclosed embodiments.

Listed below are non-limiting embodiments A1-A24.

A1. Fibers comprising one or more identification fibers, wherein each of the identification fibers exhibits at least one distinct feature, wherein the identification fibers comprise one or more branded fibers, wherein the branded fibers exhibit the distinct features comprising one or more taggant surface markings, wherein the taggant surface markings form a repeated pattern along a length of the branded fibers, and wherein the taggant surface markings and/or repeated pattern is representative of a code of the fibers.

A2. The fibers of embodiment A1, further comprising standard fibers and wherein the code is representative of at least one supply chain component of the fibers or the standard fibers.

A3. The fibers of any of embodiments A1 or A2, wherein the repeated pattern comprises an alphanumeric code, a digital code, an analog code, or an ideographic code.

A4. The fibers of embodiment A1, wherein the repeated pattern includes metadata.

A5. The fibers of embodiment A4, wherein the metadata comprises a read-start position, a read-end position, a read direction, spacing of the digits within the code.

A6. The fibers of any of embodiments A3-A5, wherein the repeated pattern comprises a digital code and wherein the digital code comprises a binary code.

A7. The fibers of embodiment A6, wherein a number of digits in the binary code ranges from 2 to 500, 4 to 100 10 to 100, 20 to 100, 4 to 50, 10 to 50, or 20 to 50.

A8. The fibers of any of embodiments A1-A7, wherein the length of the repeated pattern ranges from 2 mm to 500 mm, 2 to 200 mm, 2 to 30 mm, 5 mm to 200 mm, 5 mm to 30 mm, 10 to 200 mm, or 10 to 30 mm.

A9. The fibers of any of embodiments A1-A8, wherein the repeated pattern is essentially one-dimensional.

A10. The fibers of any of embodiments A1-A9, wherein the repeated pattern is printed on the branded fibers.

A11. The fibers of any of embodiments A1-A9, wherein the repeated pattern is imparted on the branded fibers by engraving or morphology modification.

A12. The fibers of any of embodiments A2-A11, wherein the standard fibers comprise cellulose acetate.

A13. The fibers of any of embodiments A2-A12, wherein the branded fibers are essentially insoluble in a solvent, wherein the standard fibers are soluble in the solvent.

A14. The fibers of any of embodiments A12 or A13, wherein the branded fibers are essentially insoluble in acetone or methylene chloride.

A15. The fibers of any of embodiments A12-A14, wherein the branded fibers are essentially not susceptible to solvent bonding with triacetin.

A16. The fibers of any of embodiments A1-A15, where in the branded fibers comprise acrylic, modacrylic, aramid, nylon, polyester, polypropylene, rayon, polyacrylonitrile, polyethylene, cellulose triacetate, or PTFE.

A17. The fibers of any of embodiments A2-A16, wherein the at least one supply chain component comprises a manufacturer of the standard fibers, a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a fiber band comprising the fibers, a manufacturing site of the fiber band, a manufacturing line of the fiber band, a production run of the fiber band, a production date of the fiber band, a package of the fiber band, a warehouse of the fiber band, a customer of the fiber band, a ship-to location of the fiber band, a manufacturer of an article comprising the fibers, a manufacture site of the article, a manufacturing line of the article, a production run of the article, a production date of the article, a package of the article, a warehouse of the article, a customer of the article, or a ship-to location of the article.

A18. An acetate tow band comprising fibers, comprising the fibers of any of embodiments of any of A2-A17, wherein the standard fibers comprise cellulose acetate.

A19. The acetate tow band of embodiment A18, wherein the at least one supply chain component comprises a manufacturer of a acetate tow band, a manufacturing site of the acetate tow band, a manufacturing line of the acetate tow band, a production run of the acetate tow band, a production date of the acetate tow band, a bale of the acetate tow band, a warehouse of the acetate tow band, a customer of the fiber band, or a ship-to location of the acetate tow band.

A20. The acetate tow band of any of embodiments A18 or A19, wherein the at least one supply chain component comprises the bale of the acetate tow band.

A21. A method of making an acetate tow band comprising fibers of any of embodiments A2-A17, wherein the method comprises: (a) obtaining the identification fibers (b) producing the standard fibers on a first fiber production process; and (c) combining the identification fibers and the standard fibers into the acetate tow band.

A22. The method of embodiment A21, wherein the obtaining of the identification fibers comprising the branded fibers comprises at least one of (i) the producing the portion of the identification fibers on the second fiber production process followed by applying the taggant surface markings in the repeated pattern to the identification fibers to produce a portion of the branded fibers; (ii) receiving the portion of the identification parties from the third party followed by applying the taggant surface markings in the repeated pattern to the identification fibers to produce a portion of the branded fibers; or (ii) receiving a portion of the branded fibers from the third party.

A23. The method of embodiment A22, wherein applying the taggant surface markings in the repeated pattern comprises engraving, printing, or morphological modification.

A24. The method of embodiment A22, wherein the applying comprises printing the taggant surface markings in the repeated pattern on the branded fibers concurrently to producing the standard fibers and combining the branded fibers and the standard fibers before crimping the acetate tow band.

A25. The method of embodiment A21, wherein the applying comprises laser engraving the taggant surface markings in the repeated pattern on the branded fibers concurrently to producing the standard fibers and combining the branded fibers and the standard fibers before crimping the acetate tow band.

A26. A method of characterizing a fiber sample, wherein the fiber sample comprises fibers of any of embodiments A2-A17, wherein the method comprises (1) optionally, separating the branded fibers from the fiber sample, (2) applying imaging technology to the branded fibers, and (3) determining the repeated pattern of the taggant surface markings.

A27. The method of embodiment A26, wherein the separating comprises placing the fiber sample in a solvent to produce a solution comprising a dissolved portion of the fiber sample and the branded fibers and removing the branded fibers from the solution.

A28. The fibers of any of embodiments A26 or A27, wherein the standard fibers comprise cellulose acetate, wherein the fiber sample comprises a portion of an article comprising the fibers, and wherein the article is selected from the group consisting of a filter rod and a cigarette filter.

A29. The fibers of any of embodiments A26 or A27, wherein the fiber sample comprises a portion of an article comprising the fibers, and wherein the article is selected from the group consisting of fabrics and other textile products, non-wovens, and absorbent products A30. The fibers of any of embodiments A26-A29, wherein the imaging technology is selected from the group consisting of human visual inspection, microscopy, electron microscopy, confocal microscopy, and optical scanning.

A31. The fibers of any of embodiments A26-A29, further comprising correlating the taggant surface markings and the repeated pattern to a database comprising manufacture specific taggants and determining the at least one supply chain component, wherein the at least one supply chain component comprises a manufacturer of the standard fibers a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a fiber band comprising the fibers, a manufacturing site of the fiber band, a manufacturing line of the fiber band, a production run of the fiber band, a production date of the fiber band, a package of the fiber band, a warehouse of the fiber band, a customer of the fiber band, a ship-to location of the fiber band, a manufacturer of an article comprising the fibers, a manufacture site of the article, a manufacturing line of the article, a production run of the article, a production date of the article, a package of the article, a warehouse of the article, a customer of the article, or a ship-to location of the article.

A32. The method of embodiment A31, wherein the fiber sample comprises a portion of a filter, wherein the filter comprises an acetate tow band, and wherein the at least one supply chain component comprises a bale of the acetate tow band.

EXAMPLES

Example 1

Nylon monofilament of 0.28 mm diameter was printed using an ID Technologies® Ci3300 inkjet printer with the code and settings in FIG. 2 entered into the printer's graphic design utility. The ink used was an acetone-based proprietary formulation provided by ID Technologies®. The printed coding was applied on a continuous basis as the nylon monofilament was wound onto a spool as is typical in the production of cellulose acetate yarn. The printer head was placed above the fiber such that the printed bars were perpendicular to the fiber and the fiber's moving direction, ensuring that the ink contacted the fiber. The approximate 1 mm spacing between the resulting print marks on the fiber was obtained by adjusting the width setting on the printer (which controls the time gap between when the bars are printed) and the speed of the fiber (i.e. the surface speed of the winder). Approximately 1000 m of encoded or branded fiber was produced.

The spool of encoded nylon monofilament was withdrawn from its package and fed into the tow band of a cellulose acetate tow production process prior to the crimper. The cellulose acetate tow was a typical commercial, "Y" cross section tow item with a nominal 2.8 filament denier and 31,000 total denier. The tow with the encoded monofilament was crimped, conditioned and delivered to a baler using standard manufacturing conditions. The tow was not compressed per typical bailer operations.

Figure 3A:
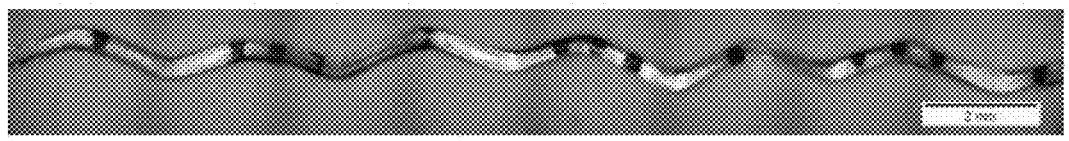
FIG. 3A shows a photomicrograph of a branded nylon monofilament that has been recovered from a filter rod and 3B shows a photomicrograph of a branded polyester thread that has been recovered from a crimped acetate tow band.

Filter rods were produced from the tow on an AF2N plug maker at a tape speed of 300 m/m, forming a filter rod of 120 mm in length of typical tow weights and Triacetin plasticizer levels used in the tobacco industry. The encoded fiber was manually extracted from rods and inspected with a microscope. The printed information remained readily detectable and quantifiable. FIG. 3a shows a stitched image of a fiber extracted from a filter rod made with the tow containing the encoded fiber. Spacing and clarity of code is typical of all samples similarly generated.

Example 2

Example 1 was repeated using a Polypropylene monofilament of 0.2 mm diameter. Although, as with Example 1, the coded monofilament was incorporated into the tow band and processed into a filter rod successfully, the printing ink did not adhere well to the fiber substrate, resulting in a degree of smudging and smearing such that the extracted branded fiber could not be decoded successfully. Although it is believed that a different ink and/or fiber surface modifications would improve ink adherence, no further work was performed with polypropylene fibers.

Example 3

Figure 3B:
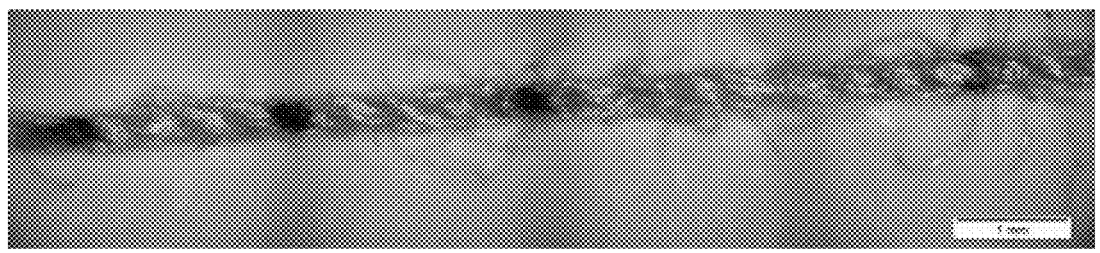

The acetate tow band production of Example 1 was repeated using a polyester thread. The encoded thread was manually extracted from the tow. As with Example 1, the encoded information remained readily detectable and quantifiable. FIG. 3b shows a stitch image of the extracted branded thread. Spacing and clarity of code is typical of all samples similarly generated.

Example 4

Figure 4:
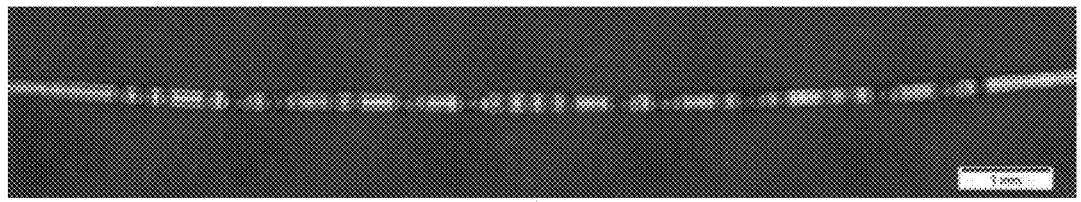
FIG. 4 shows a photomicrograph of an acrylic monofilament fiber engraved using a MACSA carbon dioxide laser

A sample of UHS (acrylic) monofilament fiber with a diameter of 0.193 mm was marked with a pattern using a MACSA carbon dioxide laser. The marked fiber is shown in FIG. 4. Although filter rods were not produced using the pictured monofilament, one skilled in the art would expect filter rod results similar to those of Examples 1 and 3.

Other embodiments will be apparent to those skilled in the art from consideration of the specification and practice of the embodiments disclosed herein. I will be understood that variations and modifications can be effected within the spirit and scope of the disclosed embodiments. It is further intended that the specification and examples be considered as exemplary only, with a true scope and spirit of the disclosed embodiments being indicated by the following claims.

We claim:

1. A method of making an acetate tow band comprising fibers, wherein the fibers comprise standard fibers and identification fibers, wherein the standard fibers comprise cellulose acetate, wherein the method comprises:
   (a) obtaining the identification fibers;
   (b) producing the standard fibers on a first fiber production process; and
   (c) combining the identification fibers and the standard fibers into the acetate tow band, wherein the identification fibers comprise one or more branded fibers, wherein the branded fibers exhibit one or more taggant surface markings,
   wherein the taggant surface markings form a repeated pattern along a length of the branded fibers, and
   wherein the taggant surface markings and the repeated pattern are representative of at least one supply chain component of the acetate tow band.

2. The method of claim 1, wherein the obtaining of the identification fibers comprising the branded fibers comprises at least one of
   (i) producing the portion of the identification fibers on a second fiber production process followed by printing or laser engraving the taggant surface markings in the repeated pattern to the identification fibers to produce a portion of the branded fibers;
   (ii) receiving the portion of the identification fibers from a third party followed by applying the taggant surface markings in the repeated pattern to the identification fibers to produce a portion of the branded fibers;
   (iii) receiving a portion of the branded fibers from the third party; or
   (iv) simultaneously producing a portion of the identification fibers on the first production process followed by applying the taggant surface markings in the repeated pattern to the identification fibers to produce a portion of the branding fibers.

3. The method of claim 2, wherein applying the taggant surface markings in the repeated pattern comprises engraving, printing, or morphological modification.

4. The method of claim 2, wherein the applying comprises printing the taggant surface markings in the repeated pattern on the branded fibers concurrently to producing the standard fibers and combining the branded fibers and the standard fibers before crimping the acetate tow band.

5. The method of claim 2, wherein the applying comprises laser engraving the taggant surface markings in the repeated pattern on the branded fibers concurrently to producing the standard fibers and combining the branded fibers and the standard fibers before crimping the acetate tow band.

6. The method of claim 1, wherein the repeated pattern comprises an alphanumeric code, a digital code, an analog code, or an ideographic code.

7. The method of claim 6, wherein the repeated pattern includes metadata and wherein the metadata comprises a read-start position, a read-end position, a read direction, and/or spacing of the digits within the code.

8. The method of claim 6, wherein the repeated pattern comprises a digital code and wherein the digital code comprises a binary code.

9. The method of claim 8, wherein a number of digits in the binary code ranges from 2 to 500 and wherein the length of the repeated pattern ranges from 2 to 200 mm.

10. The method of claim 1, wherein the branded fibers are essentially insoluble in a solvent wherein the standard fibers are soluble in the solvent and wherein the branded fibers are essentially not susceptible to solvent bonding with triacetin.

11. The method of claim 1, wherein the at least one supply chain component comprises at least one of a manufacturer of the acetate tow band, a manufacture site of the acetate tow band, a manufacturing line of the acetate tow band, a production run of the acetate tow band, a production date of the acetate tow band, a bale of the acetate tow band, a warehouse of the acetate tow band, a customer of the acetate tow band, or a ship-to location of the acetate tow band.

12. The method of claim 11, wherein the at least one supply chain component comprises the bale of the acetate tow band.

13. A method of making an acetate tow band comprising fibers, wherein the fibers comprise standard fibers and identification fibers, wherein the standard fibers comprise cellulose acetate, wherein the method comprises:
(a) producing standard fibers on a first fiber production process;
(b) obtaining identification fibers;
(c) applying taggant surface markings in a repeated pattern on the identification fibers to produce branded fibers; and
(d) combining the branded fibers and the standard fibers to form the acetate tow band;
wherein, steps (a) and (c) occur concurrently and step (d) occurs prior to crimping the acetate tow band, and
wherein the taggant surface markings and the repeated pattern are representative of at least one supply chain component of the acetate tow band.

14. The method of claim 13, wherein the applying comprises laser engraving or printing.

15. The method of claim 13, wherein the repeated pattern is essentially one dimensional.

16. The method of claim 13, wherein the repeated pattern includes metadata and wherein the metadata comprises a read-start position, a read-end position, a read direction, and/or spacing of the digits within the code.

17. The method of claim 16, wherein a number of digits in the binary code ranges from 2 to 500 and wherein the length of the repeated pattern ranges from 2 to 200 mm.

18. The method of claim 13 wherein the repeated pattern comprises a digital code and wherein the digital code comprises a binary code.

19. The method of claim 13, wherein the at least one supply chain component comprises the manufacturer of the acetate tow band and the customer of the acetate tow band.

20. The method of claim 13, wherein the at least one supply chain component comprises the bale of the acetate tow band.

* * * * *